(12) United States Patent
Oda et al.

(10) Patent No.: US 7,223,726 B2
(45) Date of Patent: May 29, 2007

(54) APOLIPOPROTEIN A-I MUTANT PROTEINS HAVING CYSTEINE SUBSTITUTIONS AND POLYNUCLEOTIDES ENCODING SAME

(75) Inventors: Michael N. Oda, Benicia, CA (US); Trudy M. Forte, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 460 days.

(21) Appl. No.: 10/342,965

(22) Filed: Jan. 14, 2003

(65) Prior Publication Data

US 2003/0181372 A1 Sep. 25, 2003

Related U.S. Application Data

(60) Provisional application No. 60/348,683, filed on Jan. 14, 2002.

(51) Int. Cl.
C07K 14/775 (2006.01)
(52) U.S. Cl. .......................................... 514/2; 530/359
(58) Field of Classification Search ..................... None
See application file for complete search history.

(56) References Cited

U.S. PATENT DOCUMENTS

| | | | |
|---|---|---|---|
| 5,691,196 A | 11/1997 | Mak et al. | |
| 5,700,650 A | 12/1997 | Mak et al. | |
| 5,721,114 A | 2/1998 | Abrahamsen et al. | |
| 5,876,968 A | 3/1999 | Sirtori et al. | |
| 6,258,596 B1 | 7/2001 | Benoit et al. | |
| 6,367,479 B1 | 4/2002 | Williams | |
| 6,391,298 B1 | 5/2002 | Radtke | |

FOREIGN PATENT DOCUMENTS

WO   WO 96/37608   * 11/1996

OTHER PUBLICATIONS

Bergeron et al. 'Characterization of Human Apoliporotein A-I Expressed in *Escherichia coli*.' Biochemica et Biophysica Acta. vol. 1344, pp. 139-152. 1997.*
Aviram M et al., Paraoxonase Inhibits High-density Lipoprotein Oxidation and Preserves its Functions: A possible peroxidative role for paraoxonase. J. Clin. Invest. 101 (8): 1581-1590 (1998).
Ayub A et al., Serum Paraoxonase after Myocardial Infarction. Arterioscler Thromb Vasc Biol. 1999; 19:330-335.
Bhalchandra J Kudchodkar et al., Dietary Fat Modulates Serum Paraoxonase 1 Activity in Rats. J. Nutr. 130:2427-2433 (2000).
Bielicki J and Oda M, Apolipoprotein A-IMilano and Apolipoprotein A-IParis Exhibit an Antioxidant Activity Distinct from That of Wild-Type Apolipoprotein A-I. Biochemistry 41:2089-2096 (Jan. 16, 2002).

Bruckert E et al., The replacement of arginine by cysteine at residue 151 in Apolipoprotein A-I produces a phenotype similar to that of Apolipoprotein A-I Milano. Artherosclerosis 128 (1997) 121-128.
Frank E et al., Paraoxonase and its Role in Cardiovascular Disease. eJIFCC vol. 13, No. 2 at http://www.ifcc.org/ejifcc/vol13no2/1301200102.htm.
Graham A et al., Evidence for a paraoxonase-independent inhibition of low-density lipoprotein oxidation by high-density lipoprotein. Atherosclerosis 135 (1997) 193-204.
James RW et al. Modulated serum activities and concentration of paraoxonase in high density lipoprotein deficiency states. Atherosclerosis 139 (1998) 77-82.
Mackness B et al., Human Serum Paraoxonase. Gen. Pharmac. vol. 31, No. 3, pp. 329-336, 1998.
Oda M et al., Cysteine Substitutions in Apolipoprotein A-I Primary Structure Modulate Paraoxonase Activity. Biochemistry 40, 1710-1718 (Jan. 19, 2001).
Oda M et al.. Paraoxonase 1 Overexpression in Mice and its Effect on High-Density Lipoproteins. Biochem and Biophys Res Communications 290, 921-927 (2002).
Pruzanski W et al., Comparative analysis of lipid composition of normal and acute-phase high density lipoproteins. J. Lipid Res. 2000. 41:1035-1047.
Rodrigo L et al., Hydrolysis of platelet-activating factor by human serum paraoxonase. Biochem. J. (2001) 354: 1-7.
Rosenblat M et al., Serum Paraoxonase Activity and the Extent of Lipid Peroxidation Are not Affected by Increased Levels of Human Apolipoprotein A-I: Studies in Transgenic Mice. Biochemistry 41:2089-2096 (Jan. 16, 2002).
Ryan R et al., Optimized bacterial expression of human apolipoprotein A-I. Protein Expression and Purification 27 (2003) 98-103.
Sirtori CR et al., Recombinant apolipoproteins for the treatment of vascular diseases Atherosclerosis 143 (1999) 29-40.
Tilly-Kiesi M et al., Subjects with ApoA-I(Lys107-->0) exhibit enhanced fractional catabolic rate of ApoA-I in Lp(AI) and ApoA-II in Lp(AI with AII). Arterioscler Thromb Vasc Biol. May 1997;17(5):873-80.
Valabhji J et al., High-density lipoprotein composition and paraoxonase activity in Type 1 diabetes. Clinical Science (2001) 101, 659-670.

* cited by examiner

*Primary Examiner*—Anish Gupta
(74) *Attorney, Agent, or Firm*—Lawrence Berkely National Laboratory; Michelle Chew Wong; Fernando Santos

(57) ABSTRACT

Functional Apolipoprotein A-I mutant proteins, having one or more cysteine substitutions and polynucleotides encoding same, can be used to modulate paraoxonase's arylesterase activity. These ApoA-I mutant proteins can be used as therapeutic agents to combat cardiovascular disease, atherosclerosis, acute phase response and other inflammatory related diseases. The invention also includes modifications and optimizations of the ApoA-I nucleotide sequence for purposes of increasing protein expression and optimization.

13 Claims, 6 Drawing Sheets

FIGURE 2

```
↓1/--                              Nsi I              ↓31/-7        Factor Xa Cleavage Site
ggt acc aaa agc tgg cat ATG CAT CAC CAT CAC CAT CAC ATC GAA GGT CGT|GAc GAg CCa
└─Kpn I─┘           └─────┘ M   H   H   H   H   H   H   I   E   G   R | D   E   P
                     Nde I ↓61/4           O               O               O   ↓91/14      O               O               O
CCg CAG AGt CCg TGG GAT CGc GTG AAG GAC CTG GCC ACT GTG TAC GTG GAT GTG CTC AAA
 P   Q   S   P   W   D   R   V   K   D  └L   A ┘T   V   Y   V   D   V   L   K
                                         Bal I/Msc I ↓121/24          O                   O               O   ↓151/34              O
GAC AGC GGC cGc GAC TAT GTG TCt CAG TTT GAA GGa TCC GCC TTG GGA AAA CAG CTg AAC
 D   S  └G   R┘ D   Y   V   S   Q   F   E  └G   S┘  A   L   G   K   Q   L   N
          Ava I/Not I                       BamH I ↓181  O              O                ↓O211/54           O               O
CTt AAG CTC CTT GAC AAC TGG GAC AGC GTG ACC TCC ACC TTC AGC AAG CTG CGC GAA CAG
└L   K┘ L   L   D   N   W   D   S   V   T   S   T   F   S   K   L   R   E   Q
 Afl II ↓241/64                                         ↓271/74
CTC GGC CCT GTG ACC CAG GAa TTC TGG GAT AAC CTg GAA AAG GAG ACA GAG GGC CTG cGc
 L   G   P   V   T   Q  └E   F┘ W   D   N   L   E   K   E   T   E   G   L   R
                         EcoR I ↓301/84                                ↓331/94  O
CAG GAG ATG AGC AAG GAT CTG GAG GAG GTG AAG GCC AAG GTG CAG CCg TAC CTG GAC GAC
 Q   E   M   S   K   D   L   E   E   V   K   A   K   V   Q   P   Y   L   D   D ↓361/104                              ↓391/114                                    O
TTC CAG AAG AAG TGG CAG GAG GAG ATG GAG CTC TAC CGC CAG AAG GTG GAG CCG CTG CGC
 F   Q   K   K   W   Q   E   E   M  └E   L┘ Y   R   Q   K   V   E   P   L   R
                                      Sac I ↓421/124                     O              ↓451/134
GCA GAG CTg CAg GAG GGC GCG CGC CAG AAG CTG CAC GAG CTG CAA GAG AAG CTG AGC CCA
 A   E  └L   Q┘ E   G   A   R   Q   K   L   H   E   L   Q   E   K   L   S   P
         Pst I ↓481/144                         O              ↓511/154
CTG GGC GAG GAG ATG CGC GAC CGC GCG CGC GCC CAT GTc GAC GCG CTG CGC ACG CAT CTG
 L   G   E   E   M   R   D   R   A   R   A   H  └V   D┘ A   L   R   T   H   L
                                                  Sal I ↓541/164                                 O   ↓571/174
GCC CCg TAC AGC GAC GAG CTG CGC CAG CGC TTG GCC GCG CGC CTT GAG GCT CTC AAG GAG
 A   P   Y   S   D   E   L   R   Q   R   L   A   A   R   L   E   A   L   K   E ↓601/184                                        ↓631/194
AAC GGC GGg GCC cGc CTG GCC GAG TAC CAC GCC AAG GCC ACC GAG CAT CTG AGC ACG CTC
 N   G  └G   A┘ R   L   A   E   Y   H   A   K   A   T   E   H   L   S   T   L
         Apa I ↓661/204                                        ↓691 O
AGC GAG AAG GCC AAG CCg GCG CTC GAG GAt CTg CGC CAg GGC CTG CTG CCg GTG CTG GAG
 S   E   K   A   K   P   A  └L   E┘ D   L   R   Q   G   L   L   P   V   L   E
                              Xho I ↓721/224                                        ↓751/234              O
AGC TTC AAG GTC AGC TTC CTG AGC GCT CTg GAa GAG TAC ACT AAG AAG CTt AAC ACC CAG
 S   F   K   V   S   F   L   S   A  └L   E┘ E   Y   T   K └K   L┘ N   T   Q
                                    ΔXho I                 Hind III ↓781/244                          ↓811/--
TGA ggc gct cta gaa cta gta gat ctg cgg ccg c
 *     └──┘    └──┘    └──┘    └────┘
        Xba I   Spe I   Bgl II   Not I
```

APOLIPOPROTEIN A-I MUTANT PROTEINS HAVING CYSTEINE SUBSTITUTIONS AND POLYNUCLEOTIDES ENCODING SAME

CROSS-REFERENCE TO RELATED APPLICATIONS

This applications claims priority to U.S. Ser. No. 60/348,683, filed Jan. 14, 2002, the contents which are hereby incorporated by reference in their entirety for all purposes.

STATEMENT REGARDING SEQUENCE LISTING

Applicants assert that the attached paper copy of the Sequence Listing for the utility application, "Apolipoprotein A-I Mutant Proteins Having Cysteine Substitutions and Polynucleotides Encoding Same," claiming priority to U.S. Provisional Patent Application No. 60/348,683, filed on Jan. 14, 2002, is identical to the Sequence Listing in computer readable form found on the accompanying computer disk, as required by 37 CFR 1.821(c) and is hereby incorporated by reference in its entirety.

STATEMENT OF GOVERNMENT SUPPORT

This invention was made during work partially supported through the U.S. Department of Energy under Contract No. DE-AC03-76SF00098. The government has certain rights in this invention.

BACKGROUND OF THE INVENTION

1. Field of the Invention

This invention generally relates to the field of HDL-associated proteins and paraoxonase activity. More specifically, the invention provides a method of modulating paraoxonase activity using apolipoprotein A-I mutant peptides having cysteine substitutions and polynucleotides encoding same. The invention has further application in the fields of treating and preventing cardiovascular diseases.

2. Description of the Related Art

Elevated HDL concentration has been correlated with a reduced risk for coronary artery disease (CAD). HDL particles are thought to possess the ability to attenuate the initiation and progression of atherosclerotic lesions. It has been proposed that the protective effects of HDL are related, in part, to its ability to inhibit the formation of minimally oxidized LDL, thus preventing the accumulation of proinflammatory mediators associated with the onset of atherogenesis. This antioxidative activity is ascribed to the enzyme, Paraoxonase (PON), which is exclusively transported on plasma HDL. HDL-associated PON possesses peroxidase-like activity that can likely protect against lipoprotein oxidation.

Human paraoxonase (PON or PON1A) is a 43 kDa glycoprotein with a broad specificity class A esterase activity (La Du, B. N., et al., (1993) *Chem Biol Interact* 87, 25–34), capable of hydrolyzing a broad spectrum of organophosphate substrates and a number of aromatic carboxylic acid esters (Gan, K. N., Smolen, A., Eckerson, H. W., and La Du, B. N. (1991) *Drug Metab Dispos* 19, 100–6.).

Recent studies suggest that this enzyme's arylesterase activity can hydrolyze bioactive oxidized phospholipids (Watson, A. D., et al., (1995) *J Clin Invest* 96, 2882–91). In vitro studies by Mackness et al. (*Atherosclerosis* (1993) 104, 129–35) have demonstrated that HDL with PON is capable of attenuating the production of lipid hydroperoxides on LDL and the formation of minimally oxidized LDL.

In PON knockout mice there is an accumulation of lipid hydroperoxides on LDL, and these mice are more susceptible to diet-induced atherogenesis (Shih, D. M., et al., Nature 394, 284–7, 1998). Furthermore, in humans, low concentrations of PON in plasma have been correlated with an increased risk for CAD (McElveen, J., et al., (1986) *Clin Chem* 32, 671–3. 11; Navab, M., et al., (1997) *J Clin Invest* 99, 2005–19). Such studies suggest an important role for HDL-PON in the protection of LDL from oxidation and the concomitant protection of the artery wall from atherogenesis. It is likely that increased transport and/or stability of the PON enzyme on HDL increases HDL's protective properties.

Apolipoprotein A-I is the major structural protein on HDL. It consists of a series of amphipathic helices that are functionally important for protein-lipid interactions as well as protein-protein interactions. The carboxy terminus of ApoA-I has high lipid-binding capacity, while the amino terminus has limited lipid-binding capacity but may be important in protein-protein interaction (Frank, P. G., and Marcel, Y. L. (2000) *J. Lipid Res.* 41, 853–72.). ApoA-I is largely responsible for mediating HDL assembly and is a determinant of HDL structure and composition.

The presence of a cysteine mutations in Apolipoprotein A-I protein at positions 151 and 173 are known in the art for their anti-atherogenic chracteristics. The ApoA-I$_{Milano}$ mutation (R173C) was first described by Franceschini G., et al., *J Clin Invest* 1980; 66:892–900. Carriers of the ApoA-I$_{Milano}$ trait characterized by the presence of a sulfhydryl group in ApoA-I (Arg173→Cys mutation) have substantial reductions in ApoA-I (approximately 50%) but have no predisposition for CAD (Franceschini, G., et al., (1980) *J Clin Invest* 66, 892–900). These patients have PON mass and activity similar to normal subjects. Sirtori et al., in U.S. Pat. No. 5,876,968, describe a pharmacological composition comprising the disulfide bonded dimer of Apolipoprotein AI$_{Milano}$ in a substantially pure form, and methods of making and purifying the dimer. Abrahamsén et al., in U.S. Pat. No. 5,721,114, describe an expression system and methods of producing Apolipoprotein A-I$_{Milano}$.

Another Arg→Cys variant, Arg151→Cys (ApoA-I$_{Paris}$) (Bruckert, E., et al., (1997) *Atherosclerosis* 128, 121–8), has low HDL cholesterol and ApoA-I without increased CAD. Benoit et al., relate variants of apolipoprotein A-I comprising a cysteine at position 151 (ApoA-I$_{Paris}$) or 175 and means for expressing these variants, in U.S. Pat No. 6,258,596.

There may be direct interactions between PON and ApoA-I. Recent studies by Sorenson et al. (*Arterioscler Thromb Vasc Biol* (1999) 19, 2214–25), using recombinant WT PON and a PON mutant lacking the hydrophobic Apolipoprotein A-I and Paraoxonase Activity N-terminal domain, suggested that PON interacts with HDL primarily through interactions of this hydrophobic moiety with HDL phospholipid. ApoA-I did enhance enzyme stability, again suggesting that on the HDL particles there may be PON-ApoA-I interactions.

Despite the strong association between HDL and PON, deficiencies in HDL and ApoA-I show variable PON activity and mass. Homozygous Tangiers patients and ApoA-I$_{Pisa}$ patients have ApoA-I concentrations <5% of normal, and some of these individuals have documented coronary artery disease (Miccoli, R., *Circulation* (1996) 94, 1622–8). This condition is associated with a 60–75% decrease in PON mass and PON arylesterase activity (James, R. W., (1998)

*Atherosclerosis* 139, 77–82); potentially the reduction in PON may be a contributing factor to the coronary heart disease noted in the patients. Patients heterozygous for the Lys107→0 mutation (ApoAI$_{Helsinki}$) (Tilly-Kiesi, M., (1995) *Arterioscler Thromb Vasc Biol* 15, 1294–306) have a 30% reduction in ApoA-I and approximately 40% reduction in PON plasma concentration (James, R. W., et al., (1998) *Atherosclerosis* 139, 77–82), and some subjects have documented coronary disease.

Like ApoA-I$_{Milano}$ and ApoA-I$_{Paris}$, PON has a free sulfhydryl group, and site-directed mutagenesis has ruled out the possibility that this sulfhydryl group is part of the enzyme's esterase catalytic site (Sorenson, R. C., et al., (1995) *Proc Natl Acad Sci USA* 92, 7187–91). Potentially the presence of a Cys in ApoA-I$_{Milano}$ (and by extension ApoA-I$_{Paris}$) could alter HDL, leading to increased PON stability or activity.

BRIEF SUMMARY OF THE INVENTION

SEQ ID NO: 1 is the polynucleotide sequence encoding wild type ApoA-I protein, found under GenBank Accession No. NM__000039.1 (Breslow, J. L., et al., *Proc. Natl. Acad. Sci. U.S.A.* (1982) 79 (22), 6861–6865).

SEQ ID NO: 2 is an optimized polynucleotide sequence encoding ApoA-I protein, having a His-6 affinity tag, Factor X$_a$ protease cleavage site and the following restriction cleavage sites after the stop codon: Bcl I, Xba I, Spe I, Bgl II and Not I. The non-naturally-occurring base nucleotides of SEQ ID NO: 2 are shown in FIG. 2 as lower case letters.

SEQ ID NO: 3 is the ApoA-I wild type protein expressed from SEQ ID NO: 1, with the open reading frame from base pair 39 to 842.

SEQ ID NO: 4 is the ApoA-I protein expressed from the optimized polynucleotide SEQ ID NO: 2, having a His-6 affinity tag.

The present invention provides an isolated polynucleotide comprising a nucleic acid sequence, preferably SEQ ID NO: 1, SEQ ID NO: 2 or one substantially homologous thereto, encoding a functional mutant Apolipoprotein A-I protein whose amino acid sequence differs from an amino acid sequence of a Apolipoprotein A-I wild type protein (SEQ ID NO: 3) or engineered Apolipoprotein A-I protein (SEQ ID NO: 4) by at least one cysteine substitution in said functional mutant Apolipoprotein A-I protein at a residue selected from the group consisting of 7, 10, 13, 17, 20, 22, 27, 30, 33, 39, 45, 49, 54, 58, 61, 96, 123, 131, 151, 173, 215 or 238, preferably at the N-terminal third (amino acid residues 1 to about 80), and more preferably at residues 10, 27 and/or 61. The cysteine substitution causes the ApoA-I mutant protein to modulate paraoxonase activity. Preferably there is a specific effect on the interaction of a paraoxonase enzyme with said Apolipoprotein A-I protein, thereby increasing paraoxonase activity.

The present invention is directed to non-naturally-occurring peptides. Therefore, when a cysteine substitution at residues 151 (ApoA-I$_{Paris}$) or 173 (ApoA-I$_{Milano}$) is employed, an additional cysteine substitution is also introduced into the present functional mutant ApoA-I protein.

The present invention also provides a protein such as may be derived from an isolated polynucleotide comprising a nucleic acid sequence, preferably SEQ ID NO: 1, SEQ ID NO: 2 or one substantially homologous thereto. The Apolipoprotein A-I mutant protein has an amino acid sequence which differs from an amino acid sequence of a Apolipoprotein A-I protein (SEQ ID NO: 3 or 4) by at least one amino acid substitution as described above, preferably at a residue selected from the group consisting of 10, 27 and 61. The latter substitution replaces an arginine with a cysteine wherein said functional mutant Apolipoprotein A-I protein has a specific effect on the interaction of a paraoxonase enzyme with said functional mutant Apolipoprotein A-I protein, thereby elevating paraoxonase activity.

The isolated polynucleotide preferably encodes an affinity tag and a site specific protease cleavage site. In a specific preferred embodiment, the isolated polynucleotide encodes a His-6 affinity tag and a Factor X$_a$ cleavage site.

The functional mutant Apolipoprotein A-I protein may elevate paraoxonase (PON) activity to a level at least 10% over that of wild type Apolipoprotein A-I protein (SEQ ID NO: 3) or a synthetic Apolipoprotein A-I protein (SEQ ID NO: 4).

Increased PON activity is measured in vitro with a purified (preferably recombinant) PON enzyme and appropriate reagents and cofactors. An artificial substrate such as Paraoxon, phenyl acetate or diazoxon may be used. See, Mackness et al. Human Serum Paraoxonase, 31 *Gen. Pharmac.* 329–335 (1998). The preferred allotype of PON used is PON1, but other PON variants may also be used. Hydrolytic esterase activity in the presence or absence of the subject functional mutant ApoA-I protein is easily measured chromogenically with the preferred experimental substrates. PON activity generates a hydrolyzed substrate product with a characteristic absorbance, e.g. absorption at 270 nm with phenyl acetate as a substrate. Thus, according to the present invention, an increase in PON activity, in the presence or absence of an ApoA-I mutant protein, may be easily determined by comparing enzymatic activity and comparing it to corresponding activity in the presence of a wild-type ApoA-I protein.

The present invention also provides a method of increasing PON activity comprising administering to a patient a pharmaceutically effective dose of a functional mutant Apolipoprotein A-I protein as described above.

The administration to a patient of a pharmaceutically effective dose of a functional mutant Apolipoprotein A-I protein is preferably by oral, intravenous, infusion, rectal, inhalation, transmuscosal or intramuscular administration. The pharmaceutical composition may be prepared by the addition of known stabilizers and excipients such as described in U.S. Pat. No. 5,696,090 issued Dec. 9, 1997, to McGregor et al, U.S. Pat. No. 5,939,390 issued Aug. 17, 1999 to Flodgaard et al., and U.S. Pat. No. 5,051,406 issued Sep. 24, 1991 to Satoh et al., all of which are hereby incorporated by reference for purposes of enabling and describing suitable pharmaceutical compositions which may be adapted to include one or more ApoA-I mutant proteins of the present invention.

BRIEF DESCRIPTION OF THE DRAWINGS

FIG. 2. Modified Apolipoprotein A-I (SEQ ID NO: 2) sequence map showing the site of modification. Residues which can be substituted with cysteines are denoted, as are other features such as restriction and cleavage sites. Wild type sequence is denoted in capital letters while modified nucleotides are denoted in lower case letters. The symbol Δ denotes a deleted restriction site.

DETAILED DESCRIPTION OF THE PREFERRED EMBODIMENT

Figure 1:
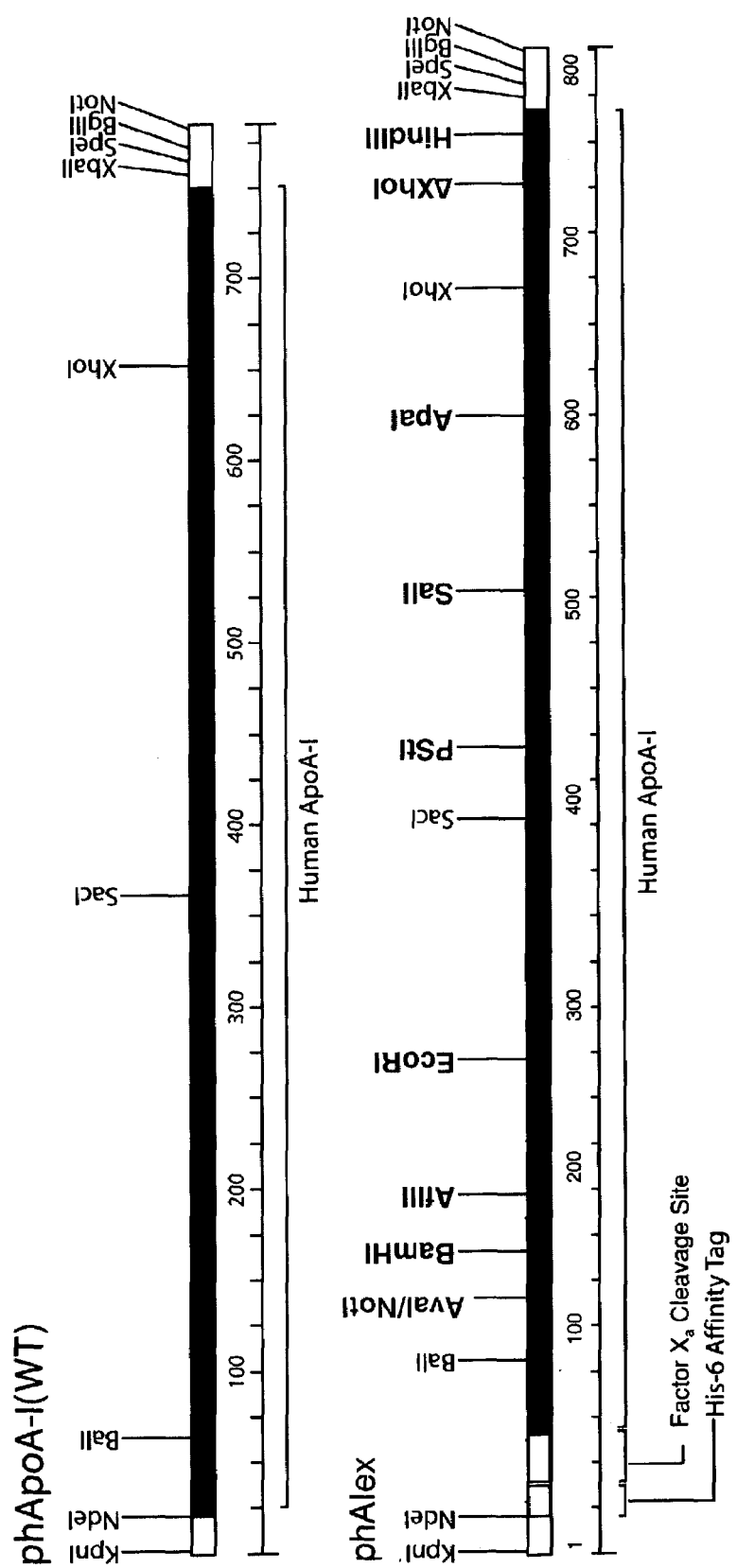
FIG. 1. Plasmid vector maps containing wild type human Apolipoprotein A-I that corresponds to SEQ ID NO: 1 (FIG. 1A) and containing modified human Apolipoprotein A-I corresponding SEQ ID NO: 2 (FIG. 1B).

Reference will now be made in detail to some specific embodiments of the invention including the best modes contemplated by the inventors for carrying out the invention. Examples of these specific embodiments are described. While the invention is described in conjunction with these specific embodiments, it will be understood that it is not intended to limit the invention to the described embodiments. On the contrary, it is intended to cover alternatives, modifications, and equivalents as may be included within the spirit and scope of the invention as defined by the appended claims.

Definitions

The term "polynucleotide" refers to a chain of nucleotides without regard to length of the chain.

The term "polypeptide" refers to a polymer of amino acids without regard to the length of the polymer; thus, peptides, oligopeptides, and proteins are included in this term.

The term "isolated" means, a polypeptide or a polynucleotide that has been cloned, synthesized or freed from its natural environment.

A polynucleotide or fragment thereof is "substantially homologous" (or "substantially similar") to another if, when optimally aligned (with appropriate nucleotide insertions or deletions) with the other polynucleotide (or its complementary strand), using BLASTN (Altschul, S. F., Gish, W., Miller, W., Myers, E. W. & Lipman, D. J. (1990) "Basic local alignment search tool." *J. Mol. Biol.* 215:403–410) there is nucleotide sequence identity in at least about 60% of the nucleotide bases, usually at least about 70%, more usually at least about 80%, preferably at least about 90%, and more preferably at least about 95–98% of the nucleotide bases. To determine homology between two different polynucleotides, the percent homology is to be determined using the BLASTN program "BLAST 2 sequences". This program is available for public use from the National Center for Biotechnology Information (NCBI) over the Internet (Tatiana A. Tatusova, Thomas L. Madden (1999), "Blast 2 sequences—a new tool for comparing protein and nucleotide sequences", *FEMS Microbiol Lett.* 174:247–250). The parameters to be used are whatever combination of the following yields the highest calculated percent homology (as calculated below) with the default parameters shown in parentheses:
Program—blastn
Reward for a match—0 or 1 (1)
Penalty for a mismatch—0, −1, −2 or −3 (−2)
Open gap penalty—0, 1, 2, 3, 4 or 5 (5)
Extension gap penalty—0 or 1 (1)
Gap x_dropoff—0 or 50 (50)
Expect—10
Word size—11
Filter—low complexity The terms "substantial homology" or "substantial identity", when referring to polypeptides, indicate that the polypeptide or protein in question exhibits at least about 30% identity using BLASTP (Altschul, S. F., Gish, W., Miller, W., Myers, E. W. & Lipman, D. J. (1990) "Basic local alignment search tool." *J. Mol. Biol.* 215:403–410) with an entire naturally-occurring protein or a portion thereof, usually at least about 70% identity over the common lengths, more usually at least about 80% identity, preferably at least about 90% identity, and more preferably at least about 90% identity or 90% positive, whichever is less. The standard BLASTP 2.2.5 defaults are used, namely "Expect 10," "Word size 3," "BLOSUM62 Matrix" and "Gap Costs Existence10, Extension 1."

The term "functional mutant" refers to a non-natural molecule that retains the essential functionality of the wild-type molecule, such as binding to a cognate partner.

The term "pharmaceutically effective dose" refers to a pharmaceutical composition or active compound of the invention that is formulated to be compatible with its intended route of administration. Such pharmaceutical composition or active compound is preferably comprised of an Apolipoprotein A-I mutant protein and a pharmaceutically acceptable carrier in dosage unit form. Dosage unit form as used herein refers to physically discrete units suited as unitary dosages for the subject to be treated; each unit containing a predetermined quantity of active compound calculated to produce the desired therapeutic effect in association with any required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals. General guidance regarding dosage and compositions is available in Remington's Pharmacautical Science by E. W. Martin, hereby incorporated by reference.

In this specification, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

Introduction

Protein-protein interactions between the human lipid-associated protein, Apolipoprotein A-I (ApoA-I) and human paraoxonase (PON) play a role in optimizing PON activity during high-density lipoprotein (HDL) assembly. PON exhibits an arylesterase activity, capable of hydrolyzing a broad spectrum of organophosphate substrates and a number of aromatic carboxylic acid esters (Gan, K. N., Smolen, A., Eckerson, H. W., and La Du, B. N. (1991) *Drug Metab Dispos* 19, 100–6.). In recent studies, it has been suggested that this enzyme can hydrolyze bioactive oxidized phospholipids (Watson, A. D., et al., (1995) *J Clin Invest* 96, 2882–91). In vitro studies by Mackness et al. (*Atherosclerosis* 104, 129–35, 1993) have demonstrated that HDL with PON is capable of attenuating the production of lipid hydroperoxides on LDL and the formation of minimally oxidized LDL.

It is known that the ApoA-I$_{Milano}$ mutation affects Apolipoprotein A-I lipid binding properties. The present invention involves the observation that the ApoA-I$_{Milano}$ variant, as well as other artificial cysteine substitution mutants of ApoA-I, modulates PON secretion and activity. HDL assembly does not appear to be required for accumulation of PON protein in the culture medium but is required for optimal PON arylesterase activity. Substitutions were made in both the N- and C-termini to determine whether the position of the Cys mutation can modulate PON activity. The results of the ApoA-I mutagenesis studies revealed that some cysteine substitutions in the N-terminal region, but not the C-terminal region, modulate PON-specific activity.

SEQ ID NO: 1 is the polynucleotide sequence encoding wild type ApoA-I protein, found under GenBank Accession No. NM_000039.1 (Breslow, J. L., et al., *Proc. Natl. Acad. Sci. U.S.A.* (1982) 79 (22), 6861–6865). SEQ ID NO: 2 is an optimized polynucleotide sequence encoding ApoA-I protein, having a His-6 affinity tag, Factor X$_a$ protease cleavage site and the following restriction cleavage sites after the stop codon: Bcl I, Xba I, Spe I, Bgl II and Not I. The non-naturally-occurring base nucleotides of SEQ ID NO: 2 are shown in FIG. 2 as lower case letters.

SEQ ID NO: 3 is the ApoA-I wild type protein expressed from SEQ ID NO: 1, with the open reading frame from base pair 39 to 842. SEQ ID NO: 4 is the ApoA-I protein expressed from the optimized polynucleotide SEQ ID NO: 2, having a His-6 affinity tag.

Accordingly, a wild type human Apolipoprotein A-I (APOAI) cDNA (SEQ ID NO: 1) is modified so that the expressed ApoA-I protein contains cysteine substitution point mutations at one or more of the following residues: 7, 10, 13, 17, 20, 22, 27, 30, 33, 39, 45, 49, 54, 58, 61, 96, 123, 131, 151, 173, 215 or 238. That is, the following mutations are introduced: P7C, R10C, D13C, V17C, D20C, L22C, R27C, V30C, F33C, G39C, K45C, N49C, T54C, S58C, R61C, K96C, R123C, R131C, R151C, R173C, R215C, and K238C. The APOAI cDNA is then subcloned into an expression vector to permit protein expression by or within a host cell. The APOAI cDNA could also be N-terminally modified to encode an affinity tag and a site specific protease cleavage site to facilitate ApoA-I mutant protein purification. The APOAI cDNA is also preferably modified by introducing silent mutations into APOAI cDNA to optimize codon usage to be compatible with the preferred host cell. See Nakamura Y, Gojobori T, Ikemura T in *Nucleic Acids Res Jan.* 1, 2000;28(1):292.

A. ApoA-I Constructs and Vectors for Optimized Expression and Purification

A preferred embodiment consists of a purified, isolated, polynucleotide that according to the nucleotide sequence of SEQ ID NO: 1 or 2, a complementary sequence or a variant that is substantially homologous thereto, provided that these polynucleotides should encode cysteine substitution mutations at one or more of the following amino acid residues: 7, 10, 13, 17, 20, 22, 27, 30, 33, 39, 45, 49, 54, 58, 61, 96, 123, 131, 151, 173, 215 or 238.

The present embodiment encompasses a recombinant vector comprising a polynucleotide that is substantially homologous to wild type APOAI (SEQ ID NO: 1) or the polynucleotide of SEQ ID NO: 2 described herein, excluding regulatory sequences and non-coding sequences and vector constructs, but including codons encoding cysteine residues at one to three locations in the polynucleotide. In a first preferred embodiment, a recombinant vector comprises expression vectors comprising either a regulatory polynucleotide of APOAI and a coding nucleic acid of the present embodiment. Within some embodiments, the expression vectors are employed in the in vivo expression of ApoA-I mutant proteins in non-human organisms. In other embodiments, the expression vectors are used for constructing transgenic animals and gene therapy.

Depending on the host organism or cell wherein the APOAI cDNA will be expressed, one skilled in the art can adapt the recombinant vector to further comprise genetic elements, including but not limited to, an origin of replication in the desired host, suitable promoters and enhancers, any necessary ribosome binding sites, polyadenylation signal, splice donor and acceptor sites, transcriptional termination sequences, selectable markers, affinity tags, cleavage sites, acid cleavage sites such as acid labile bonds between Asp-Pro residues and non-transcribed flanking sequences. Various types of gene delivery vectors can be used including, but not limited to, plasmids, YACs (Yeast Artificial Chromosomes), BACs (Bacterial Artificial Chromosomes), bacterial vectors, bacteriophage vectors, viral vectors (for example, retroviruses, adenoviruses and viruses commonly used for gene therapy), non-viral synthetic vectors, and recombinant vectors.

A second embodiment comprises a host cell that has been transformed with a human ApoA-I expression vector, such as a bacterial expression vector, herein referred to as phAIex, in particular a cysteine-encoding variant of a polynucleotide. Examples of such polynucleotides are SEQ ID NO: 1 and 2, or substantially homologous thereto, wherein the cysteine mutation at one or more of the following residues: 7, 10, 13, 17, 20, 22, 27, 30, 33, 39, 45, 49, 54, 58, 61, 96, 123, 131, 151, 173, 215 or 238. Appropriate host cells can be prokaryotic host cells, such as *E. coli, Bacillus subtilis, Salmonella typhimurium,* and strains from species including but not limited to, *Pseudomonas, Streptomyces* and *Staphylococcus*. Alternatively eukaryotic host cells can be transfected with a cysteine encoding variant of apolipoproteinA-I, including but not limited to, HeLa cells, HepG2 cells, CHO cells, BHK cells and other mammalian host cells known to be useful for recombinant protein production. A preferred embodiment is a mammalian host cell comprising the APOAI genomic region, wherein the endogenous APOAI gene is disrupted by homologous recombination with a knockout vector. Such as host cell should produce a glycosylated ApoA-I mutant protein.

To make transgenic non-human vertebrate animals, designing the construct should include as much flanking sequence of APOAI as to include all the regulatory elements that may be found in the flanking genomic DNA. One needs to consider the neighboring genes and whether or not their expression should be modified as well. See Thomas, K. R. and Capecchi, M. R., Site-directed mutagenesis by gene targeting in mouse embryo-derived stem cells. *Cell* 51:503, 1987.

In order to effect expression of the polynucleotides and polynucleotide constructs of the preferred embodiment, these constructs must be delivered to the host cell, where once it has been delivered to the cell, it may be stably integrated into the genome of the host cell and effectuate cellular expression. This delivery can be accomplished in vitro, for laboratory procedures for transforming cell lines, or in vivo or ex vivo, for the creation of therapies or treatments of diseases. Mechanisms of delivery include, but are not limited to, viral infection (where the expression construct is encapsulated in an infection viral particle), other non-viral methods known in the art such as, calcium phosphate precipitation, DEAE-dextran, electroporation, direct micro-injection, DNA-loaded liposomes, and receptor-mediated transfection of the expression construct. In a preferred embodiment, the delivery of the construct is by microinjection into the appropriate host cell or by intravenous injection in the organism.

In a specific preferred embodiment, the ApoA-I cDNA is SEQ ID NO: 1 or 2, wherein the N-terminus of ApoA-I is modified with a His-6 affinity tag and a Factor $X_a$ cleavage site and then subcloned into a bacterial expression vector, such as pET-20b from Novagen, Inc. (Madison, Wis.) to produce a human ApoA-I bacterial expression vector as shown in FIG. 1A and 1B. The expression vector is then transformed into *Escherichia coli* host cells and cultured. The cells are harvested and the ApoA-I protein is recovered by purification means (e.g. using a nickel resin matrix to bind the histidine sequence affinity tag) known in the art.

In a preferred embodiment, the codon usage of the APOAI cDNA is optimized for the *E. coli* host cell chosen as shown in FIG. 2. Referring now to FIG. 2, DNA and amino acid sequences are shown for an ApoA-I molecule which is modified in accordance with the present invention. The numbering begins with the 5' untranslated end at base 1 and indicates a histine sequence beginning at base 31 and amino acid-7 (which is cleaved from the final peptide) as numbered in FIG. 2 with the arrow pointing to the base/amino acid being numbered. The shaded circles indicate the residues which are replaced by a cysteine in the present embodiments. FIG. 2 further shows various restriction sites (e.g. Nsi 1) engineered into the sequence in order to give it more manipulability. The "Factor Xa Cleavage site" is used to obtain a mature peptide beginning with the sequence D E P . . . as shown. Note that the wild type pro-ApoA-I begins approximately 23 amino acids up from the amino terminus of the preferred sequence of SEQ ID NO: 2. The small-nucleotide letters indicate where point mutations have been made. The present ApoA-I mutant proteins may be made in pre- or pro- or mature peptide form.

Silent mutations can be made to the wild type ApoA-I polynucleotide sequence (SEQ ID NO: 1), choosing the optimal codon for any given residue of the mutant/wild type ApoA-I protein in the host cell. For example, at residue 27 of the wild type ApoA-I protein, the AGA codon codes for arginine in *E. coli*. In SEQ ID NO: 2 and depicted by FIG. 2, residue 27 is the codon CGC, which also codes for arginine. The codon CGC enjoys a frequency of 19.6/1000 in a pool of tRNAs, while the wild type codon AGA has a frequency of only 3.7/1000 tRNAs, making CGC a preferred codon by *E. coli* and thus increasing the rate and speed of translation and increasing protein expression. Thus these systematic and silent mutations can be made to increase the rate and yield of protein expression in any given host cell. Note that residue 27 is also a residue that may be mutated to cysteine.

Codon usage tables of various microorganisms such as *E. coli* and *S. cerevisiae* are well-known in the art. Codon usage tables for over 6000 organisms was described by Nakamura Y, Gojobori T, Ikemura T in *Nucleic Acids Res* 2000 Jan. 1; 28(1):292. Up to date versions of these tables can be found online in the Kazusa DNA Research Institute (KDRI) Codon Usage Database compiled from GenBank Release 131.0 [Aug. 15, 2002]. A description of such mutations and optimization of the expression of ApoA-I can be found at Ryan R O, Forte T M, Oda Minn., *Protein Expr Purif* 2003 Jan. 27(1):98–103.

Furthermore, since the present ApoA-I mutant proteins require cysteine substitutions at various residues, a time-saving measure in designing such mutant proteins is to incorporate silent mutations throughout the ApoA-I DNA sequence that will result in restriction sites, or to delete some restriction sites. For example, at base pairs 130 and 132, which correspond to residue 27 of ApoA-I as shown in FIG. 2, a direct result of the A→C base pair changes results in the creation of a Ava I/Not I restriction site from base pairs 126–133. Thus, as demonstrated by the differences in sequence between wild type ApoA-I cDNA of SEQ ID NO: 1 and the modified ApoA-I cDNA of SEQ ID NO: 2, the invention contemplates the creation of silent mutations within the coding sequence which do not alter the functionality of the expressed ApoA-I protein, but increase or optimize the creation of the ApoA-I mutant proteins and their expression.

B. ApoA-I Cysteine Substitution Mutations

It is known that a number of HDL deficiency syndromes are associated with dramatic reductions in serum PON protein and activity. An exception is ApoA-$I_{Milano}$ (R173C), which does not appreciably alter PON activity (James, R. W., et al., *Atherosclerosis* (1998) 139, 77–82). It has been found that natural (R173C and R151C), as well as artificial, cysteine mutations within ApoA-I primary sequence can be systematically created to determine whether specific regions of ApoA-I are involved in supporting and modulating PON activity. Analysis of these mutations indicate that Cys substitutions within the C-terminal lipid-binding domains of ApoA-I do not alter the specific activity of PON on nascent HDL, but rather, introduction of Cys residues within the N-terminal region of ApoA-I produce significant changes in PON activity without affecting the mass of PON enzyme secreted from cells.

A region in the N-terminal portion of ApoA-I was identified, where the presence of cysteine appears to elevate PON arylesterase activity (for example, residues 10, 27, and 61) above the PON activity of ApoA-$I_{WT}$. A second site in ApoA-I at residue 96 was found where a cysteine substitution decreases ApoA-I's ability to elevate PON arylesterase activity. This ability to modulate PON activity is also assembly-dependent because nascent particles formed by the cysteine mutants when added to lipid-free PON show little increase in arylesterase activity (data not shown). A likely explanation to account for the altered PON activity in the mutant ApoA-I nascent particles is that PON and ApoA-I interact on the surface of the particles and that changes in the conformation of ApoA-I's N-terminal portion affect the nature of this interaction.

The coassembly of PON onto ApoA-I nascent particles substantially increases PON arylesterase activity. The ApoA-I mutations may alter ApoA-I's structure, thus exposing a latent PON interaction domain of ApoA-I, thereby directing PON to the HDL particle. It is likely that the nascent HDL provides PON with the proper lipid environment for enhanced enzyme activity. Furthermore, the Cys mutations suggest that the N-terminal region may be a critical domain in the proper presentation of PON's active site to the substrate, since mutations in this region modulate PON activity. The present invention is not limited to any particular mechanism, however, being generally directed to ApoA-I mutant proteins having a non-naturally occurring cysteine residue.

Because PON possesses a free sulfhydryl group, Cys substitutions in ApoA-I can be made and result in increased PON arylesterase activity, potentially through stabilization of the PON-HDL complex. Additionally, a series of mutations can be made throughout the ApoA-I molecule, including the following arginine→cysteine substitutions: R10C, R27C, R61C, R123C, R131C, R151C, R173C, R215C, and R238C. Cysteine substitutions at the following residues should also produce a specific effect on the interaction of PON and ApoA-I and increase PON activity: 7, 10, 13, 17, 20, 22, 27, 30, 33, 39, 45, 49, 54, 58, 61, 96, 151 or 173.

C. Effect of ApoA-I Cysteine Substitution Mutations on PON Arylesterase Activity Cysteine substitutions in the N-terminal third of the ApoA-I protein are shown herein to significantly elevate arylesterase activity up to approximately 30%, as in R10C, R27C, and R61C mutants compared to ApoA-I$_{WT}$ as discussed in Example 8. Conversely, the K96C mutation had an approximate 30% reduction in arylesterase activity compared to ApoA-I$_{WT}$. ApoA-I$_{Paris}$ and ApoA-I$_{Milano}$ mutations, are not different from ApoA-I$_{WT}$ in their ability to elevate secreted PON arylesterase activity over conditioned medium without ApoA-I.

Inspection of nonreduced gel profiles (not shown) suggests that differences in PON activity cannot be attributed to the degree of dimerization of the Cys substitution mutants. The increase in PON activity in the N-terminal region is also not the result of disulfide bridge formation between PON and ApoA-I, since no band corresponding to 70 kDa (expected molecular weight for an ApoA-I/PON heterodimer) was observed by SDS PAGE Western blot in Example 5. Western blots probed for both ApoA-I and PON showed no colocalization of the proteins (data not shown), corroborating this observation.

Several cysteine substitutions made within the same mutant ApoA-I protein are also contemplated by the invention if they serve to increase PON activity in even greater fold. This would be the case in ApoA-I$_{Paris}$ (151) or ApoA-I$_{Milano}$ (173), which would require an additional cysteine. However, caution may need to be used when making more than one cysteine mutation in ApoA-I as this may have the effect of decreasing PON activity due to possible intramolecular or intermolecular interactions between the sulfhydryl groups by creation of a disulfide bond. The inventors hypothesize that the free sulfhydryl groups on the ApoA-I mutant peptides of the current invention and PON stabilize the PON-HDL complex and thereby increase PON's arylesterase activity. Without the free sulfhydryl group on the ApoA-I mutant peptides, this stabilization may not occur to increase PON activity.

The effect of more than one mutation may be determined by routine experimentation according to the present teachings and examples.

D. Pharmaceutical Compositions

These ApoA-I mutant proteins make feasible the preparation and administration (either orally or intravenously) of ApoA-I variant proteins to modulate the oxidative activity of the enzyme, paraoxonase (PON). ApoA-I containing the presently suggested mutations to may be used to increase PON's oxidative activities, and thus prevent CVD in the general population.

Purification of the expressed ApoA-I mutant proteins of the invention from the host cell can be according to purification methods known in the art, and preferably by such methods as column chromatography. For example, the use of affinity tags as described earlier enables ease of purification of the expressed ApoA-I mutant protein by affinity or anion-exchange chromatography. Suitable methods for purifying ApoA-I are also described by Ageland et al., in U.S. Pat. Nos. 5,834,596 and 5,990,081, which are hereby incorporated by reference in their entirety. The processes use an agarose matrix having an immobilized compound with an end group comprising two or three nitrogen atoms bonded to a carbon atom, such as arginine, guanidine or histidine, for attaching the endotoxins to the matrix. The matrix is treated with a surfactant for releasing the ApoA or ApoE while the endotoxins remain attached to the matrix. Alternatively, the process comprises an anion-exchange matrix for attaching the ApoA and ApoE in solution to the matrix. The anion-exchange matrix is treated with a solution comprising a compound comprising two or three nitrogen atoms bonded to a carbon atom for releasing the endotoxins while the ApoA or ApoE remains attached to the matrix, and then releasing the ApoA or ApoE from the matrix.

Other purification methods are also described by Winge et al., in U.S. Pat. Nos. 6,090,921 and 6,423,830, which uses an anion-exchange chromatography gel to purify ApoA, and are hereby incorporated by reference in their entirety.

After purification, the present ApoA-I mutant proteins may be prepared according to known pharmaceutical technology. They may be administered singly or in combination, and may further be administered in combination with other cardiovascular drugs. They may be conventionally prepared with excipients and stabilizers in sterilized, lyophilized powdered form for injection, or prepared with stabilizers and peptidase inhibitors of oral and gastrointestinal metabolism for oral administration.

The effective ApoA-I mutant peptides can also be synthesized in large quantities for use in in vivo models and eventually in humans to modulate PON activity. Synthetic peptide production is relatively non-labor intensive, easily manufactured, quality controlled and thus, large quantities of the desired product can be produced quite cheaply. Similar combinations of mass produced synthetic peptides have recently been used with great success. See Patarroyo, Vaccine, 10: 175–178 (1990) which is hereby incorporated by reference. The synthetic peptides should be at least 100 amino acids long.

In a specific preferred embodiment, the ApoA-I cDNA is SEQ ID NO: 1 or 2, wherein the N-terminus of ApoA-I is modified with a His-6 affinity tag and a Factor X$_a$ cleavage site, having a selected cysteine substitution and then subcloned into a bacterial expression vector such as pET-20b from Novagen, Inc. (Madison, Wis.) to produce a human ApoA-I bacterial expression vector. The expression vector is then transformed into *Escherichia coli* host cells and cultured. The cells are harvested and the ApoA-I protein is recovered by purification means as described above and known in the art.

The known expression system for producing large quantities of the known ApoA-I$_{Milano}$ protein (up to around 4.5 g/l) as disclosed by Abrahamsén et al., in U.S. Pat. No. 5,721,114, can be used to produce large quantities of the ApoA-I mutant proteins (having additional cysteine residues) of the current invention and is hereby incorporated by reference in its entirety.

The invention also contemplates expressing multiple ApoA-I mutant proteins that elevate PON activity by more than 10% and administering them in combination in one dose.

E. Applications and Therapeutics

These ApoA-I mutant peptides make feasible the preparation and administration (either orally or intravenously) of ApoA-I variant proteins to modulate the oxidative activity of the protein, Paraoxonase. ApoA-I containing the present suggested mutations to may be used to increase PON's oxidative activities, and thus prevent CVD in the general population.

1. Cardiovascular Therapy with ApoA-I Mutant Proteins and PON

The present ApoA-I mutant proteins may also useful in preventing the acute phase response following bypass surgery and/or after myocardial infarction, by increasing PON activity. The manner of the application of ApoA-I mutant peptides would be similar to how ApoA-I is applied currently as a therapeutic agent, through intravenous infusion of large quantities of protein to patients that are undergoing acute phase response as described by Chiesa G. and Sirtori C R, *Curr Opin Investig Drugs* 2002 March; 3(3):420–6, and Sirtori, C R, et al., *Atherosclerosis* 142 (1999) 29–40, are hereby incorporated by reference in its entirety. The acute phase response is the set of immediate inflammatory responses initiated by pattern recognition molecules which induce host responses that localize the spread of infection and enhance systemic resistance to infection.

The usual cause for acute phase response is open heart surgery or stent placement. Because acute phase response is a largely pro-inflammatory event and PON is an anti-inflammatory enzyme, an increase in PON activity would be beneficial to overcoming the acute phase response. Acute phase is also a reason why a large percentage of patients that undergo open heart surgery require a second surgery. Therefore patients that undergo heart surgery should be infused with the ApoA-I mutant proteins of the invention until the patient has passed through acute phase response to lower the chance of recurrence.

Homozygous Tangiers patients and ApoA-I$_{Pisa}$ patients, whose condition is associated with a 60–75% decrease in PON mass and PON arylesterase activity, which is a potential contributory factor to their coronary heart disease, may benefit from the administration of these mutant peptides and the subsequent increase in PON activity. Likewise, patients heterozygous for the ApoAI$_{Helsinki}$ mutation in ApoA-I and patients having documented coronary disease may also benefit from administration of these ApoA-I mutant peptides and the subsequent increase in native PON activity to offset any reduction in PON plasma concentration.

ApoA-I mutant protein therapy can be combined with non-native PON. This invention can be used in combination with such methods as that described in Radtke, U.S. Pat. No. 6,391,298, and is hereby incorporated by reference in its entirety. Radtke found a mutation in PON, 192Q, that will increase its activity and suggests using PON-1, having said mutation, to decrease atheroma formation. Thus, the ApoA-I mutant proteins of the current invention may be useful in combination with the mutated PON of Radtke, to increase the activity of PON as a method of decreasing or preventing atheroma formation and thus prevent other cardiovascular diseases.

2. Gene Therapy with APOAI Mutant Nucleic Acids

The preferred embodiment also encompasses uses of the present poynucleotide having cysteine substitutions for gene therapeutics such as those described by Gabor M. Rubanyi, "The future of gene therapy," *Molecular Aspects of Medicine* 22(2001): 113–142, and is hereby incorporated by reference in its entirety. Rubanyi describes existing and future methods of gene therapy and the technical hurdles gene therapy faces in the future. An example of contemplated drug therapies of the current invention is aimed at increasing the levels of ApoA-I mutant peptides and thereby raising the activity level of native PON in any human patient suffering from or having a predisposition for cardiovascular disease. Such methods are made possible through SEQ ID NO: 1 and 2 and their cysteine variants.

Various types of gene delivery vectors can be used including, but definitely not limited to, plasmids, YACs (Yeast Artificial Chromosomes), BACs (Bacterial Artificial Chromosomes), bacterial vectors, bacteriophage vectors, viral vectors (for example, retroviruses, adenoviruses and viruses commonly used for gene therepy), non-viral synthetic vectors, and recombinant vectors. Delivery of the vector and/or construct for gene therapy in a preferred embodiment is by viral infection or injection intravenously although delivery can be by any other means as described previously.

A preferred embodiment is modelled after the method described by Tangirala R K et al., *Circulation*. 1999 Oct. 26; 100(17):1816–22, wherein the regression of atherosclerosis was induced by liver-directed gene transfer of apolipoprotein A-I in mice. The preferred embodiment contemplates a similar protocol of gene transfer as Tangirala et al. based on the same target tissue and the desire to express the ApoA-I mutant proteins endogenously in the liver. A second-generation recombinant adenovirus encoding SEQ ID NOS: 1 or 2, or a modified human APOAI cDNA substantially homologous thereto, can be constructed as described by Tsukamoto K. et al., *Journal of Lipid Research*, 1997:38, 1869–1876. Briefly, a plasmid containing modified APOAI can be linearized with an enzyme and co-transfected into cells along with adenoviral DNA isolated and digested. The cells are then overlaid with agar and incubated at 32° C. for about 15 days. Plaques positive for APOAI cDNA are subjected to a second round of plaque purification, and the recombinant adenovirus is then expanded in cells at 32° C. A null adenovirus can be constructed and expanded in an identical manner. All viruses are then purified and stored appropriately.

While much of gene therapy uses vectors as a means of delivery, other methods of delivery to the somatic cells of a patient may be utilized. The preferred embodiment also contemplates the delivery of APOAI mutant polynucleotides by encapsulation by compositions such as, hydrogels and microgels, liposomes, and other lipid or polymer carriers. Furthermore, the APOAI mutant polynucleotides can be delivered naked, without any means of receptor-mediated entry or other carrier into the patient's cells.

3. Protein Therapeutics Using ApoA-I Mutant Proteins

The ApoA-I mutant proteins of the present invention can be isolated, recombinant or synthesized, so long as the mutant proteins maintain ApoA-I functionality and modulate PON activity. In a preferred embodiment, the active ApoA-I mutant protein of SEQ ID NO: 3 or 4 is delivered to increase PON antioxidant activity.

As described previously, a method of delivery of ApoA-I mutants would be similar to how ApoA-I is applied currently as a therapeutic agent, through intravenous infusion of large quantities of protein to patients as described by Chiesa G. and Sirtori C R, *Curr Opin Investig Drugs* March 2002; 3(3):420–6, and Sirtori, C R, et al., *Atherosclerosis* 142 (1999) 29–40, are hereby incorporated by reference in their entirety.

The presently disclosed ApoA-I proteins, and fragments thereof, may be prepared according to known pharmaceutical technology. They may be administered singly or in combination, and may further be administered in combination with other cardiovascular or triglyceride-lowering drugs. They may be conventionally prepared with excipients and stabilizers in sterilized, lyophilized powdered form for injection, or prepared with stabilizers and peptidase inhibitors of oral and gastrointestinal metabolism for oral administration. They may also be administered by methods including, but not limited to, intravenous, infusion, rectal, inhalation, transmuscosal or intramuscular administration.

EXAMPLE 1

Transfection of Cells with Human PON

The human PON1A cDNA was subcloned into the pcDNA3 vector (In Vitrogen Inc., Carlsbad, Calif.). CHO-K1 cells (~400,000 cells/mL) were transfected by electroporation (10 µg of vector, 250 V, 20 ms discharge). Screening for PON1A expression was performed by diluting cells to 4–5 cells/mL and culturing in 96-well plates in McCoy's 5A medium plus 10% heat inactivated fetal bovine serum (FBS) and G418 antibiotic (800 µg/mL) as a selective agent. The media from wells containing single colonies were individually harvested, slot blotted onto nitrocellulose, and probed with anti-PON antiserum. Immunoreactive cells expressing arylesterase activity were further examined by SDS-PAGE Western blot for the expression of full-length PON1A protein (approximate molecular mass of 43 kDa). The stably transfected clone chosen for this work expressed arylesterase activity at 80 units/L.

CHO-PON cells were grown in T-175 cell culture flasks containing McCoy's 5A medium plus 10% FBS. At confluency, the cells were first rinsed three times with Hanks' balanced salt solution and then incubated for 24 hours in serum-free medium alone or in the presence of 0.5–20 µg/mL ApoA-I (WT and mutants). The harvested conditioned medium was centrifuged briefly to eliminate cellular debris and concentrated approximately 100-fold by ultrafiltration (10,000 MW cutoff) and supplemented with 0.05 mg/mL gentamicin sulfate, 1 mM benzamidine, and 1 mM $CaCl_2$. Adherent cells in the flask were harvested and protein mass was determined by Markwell's modified Lowry method (Markwell, M. A., Haas, S. M., Bieber, L. L., and Tolbert, N. E. (1978) *Anal Biochem* 87, 206–10).

EXAMPLE 2

Production of Recombinant ApoA-I Protein

Human APOAI cDNA (SEQ ID NO: 1) was modified by primer-directed mutagenesis to encode a His-6 affinity tag N-terminal extension by use of the synthetic oligonucleotide 5' ACC CAT ATG CAT CAC CAT CAC CAT CAC ATC GAA GGT CGT GAC GAG CCA CCG CAG 3'. The protein encoded by the resulting cDNA was N-terminally modified with the amino acid sequence Met-(His) 6-Ile-Glu-Gly-Arg, which encodes a His-6 affinity tag and Factor $X_a$ proteolytic cleavage site. The APOAI cDNA sequence was confirmed by dideoxy automated fluorescent sequencing and subcloned into the pET-20b bacterial expression vector, acquired from Novagen, Inc. (Madison, Wis.), to produce the human ApoA-I bacterial expression vector phAIex, shown in FIG. 1B.

The plasmid was transformed into the *Escherichia coli* strain BL21 (DE-3) pLysS. *E. coli* harboring the phAIex plasmid were grown to 0.6 $OD_{600}$ in NCZYM medium containing 100 µg/mL ampicillin and induced by the addition of IPTG (0.4 mM), and the cells were cultured for an additional 3 h at 37° C. The cells were harvested by centrifugation at 10000 g for 15 min, resuspended in B-PER bacterial protein extraction reagent (Pierce; Rockford, Ill.), and lysed by sonication. Cellular debris was removed by centrifugation at 10000 g for 15 min. Cleared lysates were mixed with an equal volume of 2× column loading buffer (40 mM $NaPO_4$, 1 M NaCl, and 6 M guanidine hydrochloride, pH 7.4) and passed through a 5 mL His-Trap chelating column (Pharmacia, Inc.) preloaded with 0.1 M $NiSO_4$. The column was washed with 25 mL of 1× loading buffer followed by 25 mL of wash buffer (20 mM $NaPO_4$ and 0.5 M NaCl, pH 7.4). ApoA-I was eluted from the column with 25 mL of elution buffer (20 mM $NaPO_4$, 0.5 M NaCl, and 0.5 M imidazole, pH 7.4) in 0.5 mL fractions. The elution profile was determined spectraphotometrically at A280 (corrected for imidazole absorbance) and the A280 peak was pooled. The pooled eluted protein was dialyzed extensively against Tris-buffered saline (TBS; 20 mM Tris and 150 mM NaCl, pH 8.0) supplemented with 1 mM benzamidine and 1 mM EDTA, filter-sterilized, and stored at 4° C. or frozen at −70° C. Phospholipid analysis carried out on the purified protein showed that it was lipid-free.

The mutations made within wild type human APOAI cDNA (SEQ ID NO: 1) were made to express the following Cys substitutions at the following residues: R10C, R27C, R61C, K96C, R123C, R131C, R151C, R173C, R215C, and K238C. These mutations were created either by primer directed PCR mutagenesis or by the Mega-Primer PCR method (Kammann, M., Laufs, J., Schell, J., and Gronenborn, B. (1989) *Nucleic Acids Res* 17, 5404). The mutations were verified by dideoxy automated fluorescent sequencing.

EXAMPLE 3

Bacterial Expression of Human PON1A for Antibody Production

The PON1A cDNA was subcloned into the pET-20b bacterial expression vector and expressed in *E. coli* as described in Example 1. Bacterially expressed human PON was found to be extremely insoluble. This property was taken advantage of by enriching human PON through a series of detergent washes. The bacterial extract was centrifuged at 10000 g for 15 min and the pellet containing human PON1A protein was retained. The pellet was resuspended in TBS and 1% Triton X-100 and recentrifuged at 10000 g for 15 min. The Triton X-100 extraction pellet was resuspended in TBS and 1% SDS and centrifuged at 10000 g for 15 min. The supernatant containing human PON1A protein was retained. The enriched solubilized human PON1A protein was analyzed by SDS-PAGE and determined to be near homogeneity (>95%). The solubilized protein was subjected to preparative SDS-PAGE and the band containing purified human PON1A was electroeluted. The protein was quantified by the method of Markwell (*Anal Biochem* 87, 206–10, 1978).

Approximately 100 µg of purified human PON1A was emulsified in Freund's complete adjuvant (Sigma, St. Louis, Mo.) and injected into a female Alpine goat; at week 4 the goat was boosted with a second injection of purified human PON1A in incomplete Freund's adjuvant. Blood was drawn at weeks 4–9 postinoculation and examined for anti-PON, using as the test antigen human PON1A isolated from plasma. The serum was isolated from the blood, supplemented with sodium azide to 0.02%, filter-sterilized, and stored at −70° C. The antiserum did not cross-react with human ApoA-I, ApoA-II, or albumin nor with mouse ApoA-I or PON.

EXAMPLE 4

Methods for Analysis of PON Arylesterase Activity

Measuring PON Activity. PON activity was measured as arylesterase activity with phenylacetate as substrate in the presence of 1 mM $CaCl_2$, as described by Gan et al, in *Drug*

*Metab Dispos* 19, 100–6 (1991), hereby incorporated by reference in its entirety. Activity was determined by monitoring the increase in absorption at 270 nm for 60 s. One unit of PON arylesterase activity is equal to 1 mmol of phenylacetate hydrolyzed per minute.

The buffer enzyme and assay was performed in 25 mM Tris-HCl, pH 8.0, 1.0 mM $CaCl_2$, with 10 mM phenyl acetate obtained from Sigma Catalog No. P-2396 (Sigma Chemical, St. Louis, Mo.) used as the PON substrate. The substrate was made fresh prior to analysis by adding 50 µL of 100% phenyl acetate to 38 mLs of $ddH_2O$. Rabbit Paraoxonase Standard was obtained and contained an activity of 472.2 U/mL. A double-beam spectrophotometer (Shimadzu) was used to observe absorption and activity.

The reference cocktail consisted of 1.8 mLs of Tris, and 0.2 mL of phenyl acetate. The reference sample was kept in the reference beam of the double beam spectraphotometer to give an indication of the degree of autolysis of phenyl acetate (it is a relatively short lived compound) and provide the spectrophotometer a measure of background production of phenol from phenylacetate.

The sample cocktails consisted of 1.8 mL Tris, 0.2 mL phenyl acetate and 5–20 µL of sample to be tested. The samples to be tested were 5–20 µL of cell-conditioned medium containing secreted PON, taken from transfected cell culture which has been incubated in the presence or absence of varying concentrations of the ApoA-I mutant proteins of Example 2. Human PON is secreted by the cells into the medium and can then be assayed. The sample cocktail and assay components were mixed in the proportions described above and inversion mixed. A double beam Shimadzu UV 1205 spectrophotometer (Shimadzu USA, Columbia, Md.) was used to determine the 270 nm absorption of each sample. The samples were immediately placed in the spectraphotometer and absorbance at 270 nm observed. The amount of enzyme present was determined was determined by multiplying the enzyme rate of 270 nm absorption increase times 1530.1. and dividing the value by the volume of the sample examined.

Isolation and Analysis of Lipidated Complexes. Complexes resulting from incubation of CHO-PON cells with ApoA-I were ultracentrifugally isolated at d=1.063–1.21 g/mL (32), by use of the TL100 ultracentrifuge (100.2 rotor) with 0.5 mL tubes. Concentrated 24 h conditioned medium (500 µL) was adjusted to d=1.063 g/mL and centrifuged at 100,000 rpm for 3.5 h at 10° C.; the top 167 µL consisting of the d<1.063 g/mL fraction was removed. The infranatant was brought to d=1.21 g/mL with NaBr and centrifuged at 100,000 rpm for 5.25 h at 10° C. The top 167 µL (d) 1.063–1.21 g/mL) fraction was removed and the remaining d>1.21 g/mL fraction collected. The fractions were dialyzed overnight against TBS (pH 7.5) supplemented with 1 mM $CaCl_2$ at 4° C. The arylesterase activity and total protein in each fraction was quantified.

SDS-PAGE and Western Blot Analyses. Proteins were visualized on precast 4-20% SDS-polyacrylamide gels (Novex, San Diego, Calif.) according to the procedure of Laemmli (Laemmli, U.K. (1970) *Nature* 227, 680–5). Wild type and Cys mutant ApoA-I were examined by SDS-PAGE on 4–20% polyacrylamide gels. The gels were loaded with 5 µg of protein/lane. For Western blot analysis, proteins were transferred to nitrocellulose. Blots were probed with antibodies specific for either human ApoA-I (mouse monoclonal antibody, Chemicon Inc.) or human PON (goat anti-sera). Formation of Cys-substituted ApoAI-PON heterodimers was assessed by the presence or absence of a 70 kDa band immunoreactive with a PON antibody.

Preparation of Reconstituted EYPC/ApoA-I Complexes. Discoidal complexes of egg yolk phosphatidylcholine (EYPC) and ApoA-I were prepared by the cholate dialysis method as described by Nichols et al. (*Biochim Biophys Acta* 750, 353–64 (1983); *J Lipid Res* 28, 719–32 35 (1987)). Briefly, EYPC, ApoA-I and sodium cholate were combined at mole ratios of 80:1:270 in 20 mM Tris-buffered (pH 8.0) saline-EDTA and incubated (4° C.) for 18–20 h. The mixture was then dialyzed extensively in this same buffer for several days to remove the sodium cholate. Nondenaturing gradient gel electrophoresis showed that this procedure resulted in the formation of a homogeneous preparation of 9.5 nm particles.

EXAMPLE 5

Expression of PON Activity in the Presence and Absence of ApoA-I

Human PON isolated from plasma is a glycoprotein of approximately 43 kDa. PON secreted into Chinese hamster ovary cell (CHO) cell medium is similar in size to the plasma PON enzyme, suggesting that PON from CHO cells is fully glycosylated. Transfected CHO cell-conditioned medium was concentrated 200-fold. A 10 µL aliquot of the concentrated conditioned medium was loaded onto a 4–20% polyacrylamide nonreduced SDS gel, transferred to nitrocellulose, and probed with goat anti-serum to human PON. Human PON isolated from plasma was run for comparison. The Western blot (not shown) demonstrated that transfected CHO cells secrete full-length PON into the medium of the same molecular weight as the major band seen in isolated human plasma PON.

It has been previously reported by Forte et al. (*J Lipid Res* 34, 317–24, (1993)), that CHO cells incubated in the presence of ApoA-I formed nascent particles with a maximum percent ApoA-I lipidation at 10 µg/mL. To confirm that the elevated PON activity was not specific to recombinant ApoA-I, ApoA-$I_{WT}$ isolated from human plasma was also examined and gave similar results (data not shown).

Figure 3A:
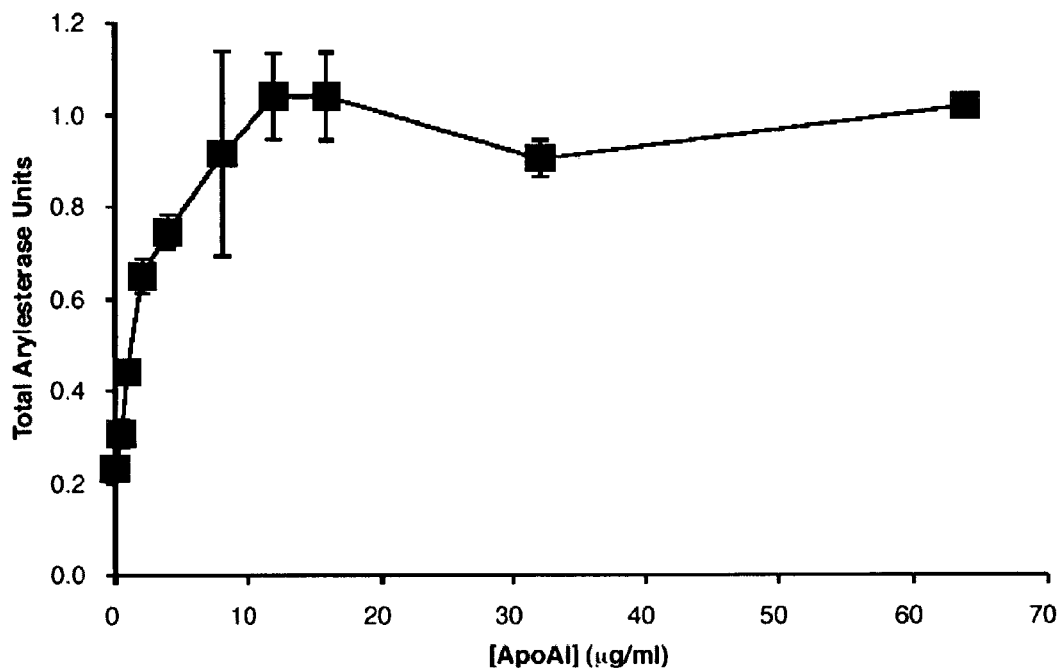
FIG. 3. Graphs showing the effect of ApoA-I on PON production and activity. The dependence of PON activity on ApoA-I concentration is shown in panel A. The time course of PON production in the absence and presence of 10 μg/mL ApoA-I is shown in panel B.

Referring now to FIG. 3A, the addition of lipid-free ApoA-I to CHO-PON cell medium results in increases in PON activity in the medium in a concentration dependent manner. The dependence of PON activity on ApoA-I concentration is shown in FIG. 3A. The secreted PON activity is maximal at approximately 12 µg/mL ApoA-I (n=4).

Figure 3B:
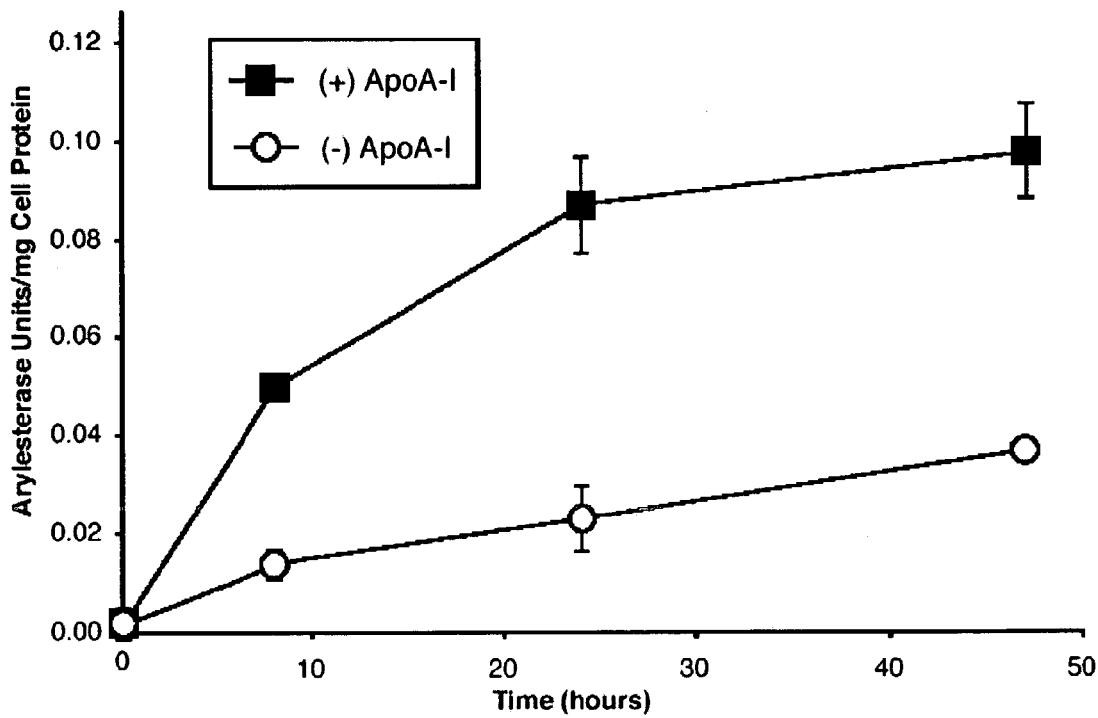

Referring to FIG. 3B, the time course of PON production in the absence and presence of 10 µg/mL ApoA-I is shown. To determine whether PON secretion was linear with time, CHO-PON cells were incubated in the absence and presence of 10 µg/mL ApoA-I for up to 48 h. Conditioned medium was collected at 0, 8, 24, and 48 h and concentrated 200-fold. PON activity was normalized to cell protein amounts. The level of PON1 arylesterase activity, as measured using the methods described in Example 4, in the cell culture medium was significantly increased in the presence of ApoA-I (n=5).

In the absence of ApoA-I, PON activity in the medium was linear over this time period; at 24 h arylesterase was 0.024±0.009 unit/mg of cell protein (n=3). In the presence of ApoA-I, there is a significant increase in PON activity in the medium; arylesterase activity at 24 h was 0.087±0.013 unit/mg of cell protein (n=3).

To ascertain whether increased PON activity reflected increased PON secretion or increased specific activity of the enzyme, an equivalent amount of total protein from concentrated conditioned medium from cells incubated in the absence of ApoA-I as well as in the presence of ApoA-I and two cysteine mutations, R61C and K96C, was loaded onto a 4–20% polyacrylamide gel, electrophoresed, transferred, and immunoprobed with anti-PON antibody. Proteins were transferred to nitrocellulose membranes and probed with antisera to human PON. Purified plasma PON was used as a standard to confirm the position of PON. The amount of PON expressed in the medium was similar whether ApoA-I was present or absent. Unique molecular weight variants of PON near 70 kDa did not arise in the presence of ApoA-I Cys mutants, suggesting that ApoA-Icys-PON covalently linked heterodimers do not form. Protein mass, as indicated by immunoreactivity to PON, was approximately the same for PON accumulating in the absence of ApoA-I as in the presence of ApoA-I, suggesting that ApoA-I increases specific activity of the enzyme and not its mass.

The presence of disulfide bond formation between Cys-substituted-ApoA-I and PON was determined demonstrating that recombinant Human ApoA-I-containing Cys substitution mutations are covalently linked dimers. The apparent molecular weights of the dimerized species differ in relation to the position of the Cys substitution. Under reducing conditions (5%, -mercaptoethanol), these proteins migrated as single bands of the same molecular weight as wild type ApoA-I, but as separate bands under non-reducing conditions. Formation of Cys-substituted ApoAI-PON heterodimer was assessed by the presence or absence of a 70 kDa band immunoreactive with a PON antibody.

Recombinant ApoA-I$_{WT}$ and Cys substituted ApoA-I mutant proteins were examined by reduced and nonreduced SDS-PAGE to assess the degree of dimerization. Under nonreducing conditions, the degree of dimerization was variable depending on the site of Cys substitution. Upon reduction, all bands migrate as a single band, indicating that the additional bands arose from conformational variants that exist in the covalently linked dimer. Additionally, the dimer form of ApoA-I Cys-containing mutants migrated with increasing apparent molecular weight up to residue 131 and with decreasing molecular weight thereafter, while not affecting the apparent molecular weight of the monomeric state. This observation suggests that the covalently linked dimer is in a more elongated conformation when the Cys is positioned centrally within the ApoA-I primary sequence, consistent with the elongated two-helix bundle model for ApoA-I lipid-free structure proposed by Rogers et al. (*Biochemistry* 37, 945–55, (1998); *Biochemistry* 37, 11714–25 (1998)).

EXAMPLE 6

ApoA-I-Induced Elevation in PON Activity.

The level of secreted arylesterase activity was significantly increased in the presence of ApoA-I (n=5). These results suggest that PON activity was dependent on the assembly of nascent HDL. However, that lipid-free ApoA-I may interact with secreted PON and independently increase activity needed to be ruled out. To differentiate between these possibilities, 24 hour concentrated conditioned medium was exposed, postculture, to lipid-free ApoA-I. The post-incubation addition of lipid-free ApoA-I to conditioned medium possessing PON activity (i.e., absence of cells) did not augment enzyme activity, whereas culturing of CHO-PON cells with ApoA-I produced a 2.1-fold increase in arylesterase activity.

Figure 4:
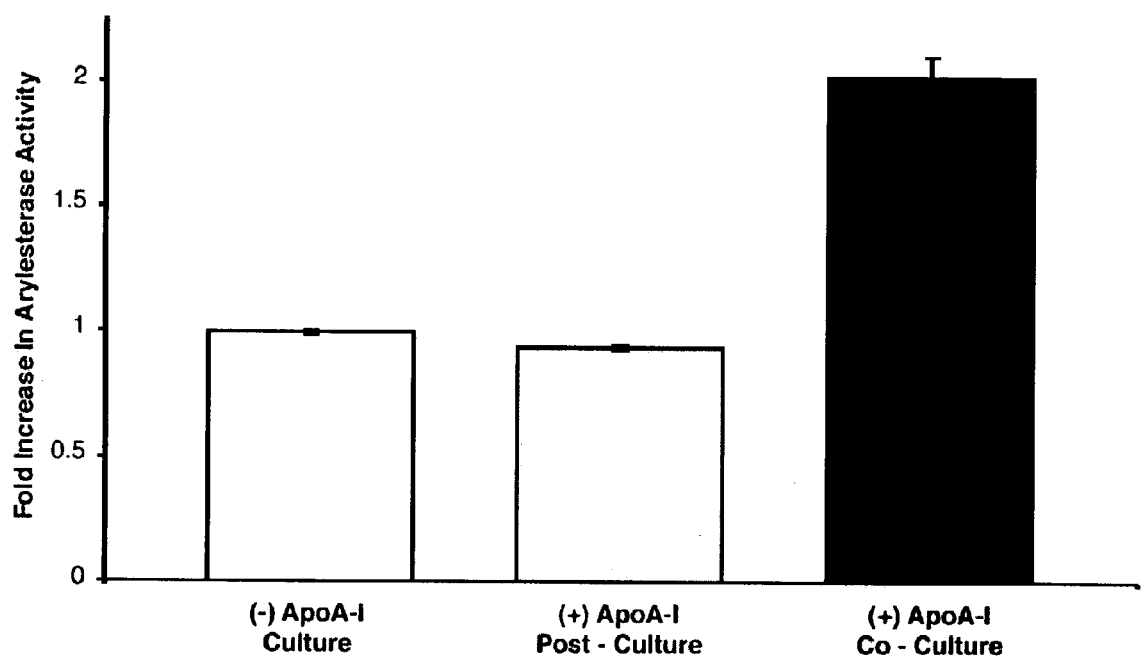
FIG. 4. Graph showing that CHO cells cultured overnight in serum-free medium in the presence (black bar) of 10 μg/mL ApoA-I exhibit a 203% ±16% increase in activity over cells grown in the absence of ApoA-I (white bar=baseline).

Referring to FIG. 4, optimal PON activity requires ApoA-I lipidation. CHO cells were cultured overnight in serum-free medium both in the absence (white bar) baseline and presence (black bar) of 10 μg/mL ApoA-I. The latter shows a 203%±16% increase in PON activity of cells grown in the presence of Apo-AI over cells grown in the absence of ApoA-I. To rule out that lipid-free ApoA-I is sufficient to increase arylesterase activity, the baseline medium was incubated for 3 h at 37° C., with 10 μg/mL ApoA-I postculture but no increase in enzyme activity was noted (gray bar, 94.4%±1.5%). Values represent the means of three experiments.

EXAMPLE 7

Distribution of PON Activity in Nascent HDL Particles Versus the Lipid-Free PON.

Figure 5:
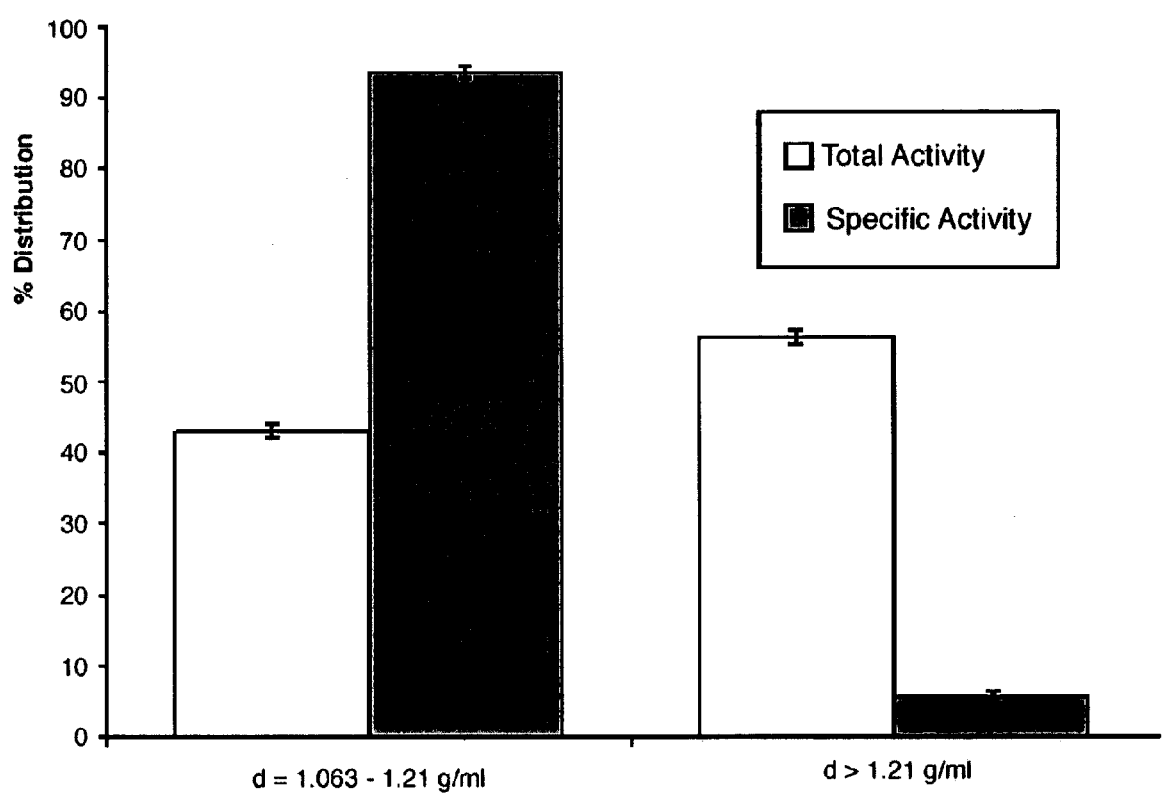
FIG. 5. Bar graph showing distribution of PON activity in nascent HDL particles versus the lipid-free fraction.

Referring now to FIG. 5, the distribution of arylesterase activity was assessed after ultracentrifugal fractionation of concentrated conditioned medium. The conditioned medium from CHO-PON cells was concentrated 200-fold and subjected to ultracentrifugal fractionation as described in Example 4. The d=1.063–1.21 g/mL and d>1.21 g/mL fractions were collected, representing the HDL and lipid-poor fractions, respectively. Total activity (white bar) and specific activity (units per milligram of protein, gray bar) were determined. Data represents the mean (standard deviation of three experiments).

A larger fraction of the PON arylesterase activity was associated with the lipid-poor d>1.21 g/mL fraction compared to the d=1.063–1.21 g/mL fractions (56.6±0.97 versus 43.4±0.97 total units, respectively). Arylesterase specific activity is nearly 15-fold higher in the HDL d=1.063–1.21 g/mL fraction compared to the d>1.21 g/mL fraction (94%±0.76% versus 6.0%±0.76%).

EXAMPLE 8

Effect of ApoA-I Mutant Proteins on PON Activity.

Figure 6:
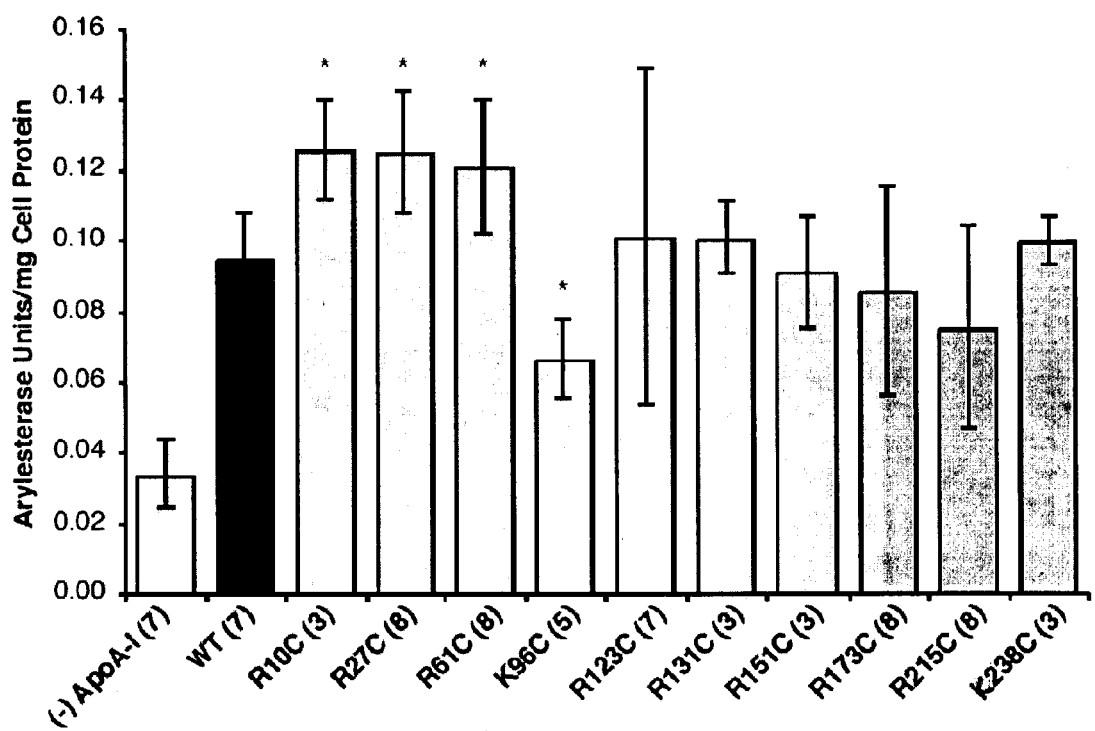
FIG. 6. Graph showing the effect of ApoA-I mutations on PON activity. CHO cells expressing PON were cultured in the absence and presence of 10 μg/mL either WT or mutant ApoA-I for 24 h.

Referring now to FIG. 6, the effect of ApoA-I mutant proteins on PON activity was investigated. Arylesterase activity is plotted on the Y-axis for a control (absent ApoA-I), ApoA-I$_{WT}$ (black bar) and ten ApoA-I mutant proteins. Because the R151C (ApoA-I$_{Paris}$) and R173C (ApoA-I$_{Milano}$) mutants may possess anti-atherogenic characteristics and the fact that they bear sulfhydryl groups, the inventors examined the possibility that Cys substitutions in ApoA-I may result in increased PON arylesterase activity, potentially through stabilization of the PON-HDL complex. A series of mutations were made throughout the ApoA-I molecule as follows: R10C, R27C, R61C, K96C, R123C, R131C, R151C, R173C, R215C, and K238C.

CHO cells expressing PON were cultured in the absence and presence of 10 μg/mL either WT or mutant ApoA-I for 24 h. The number of experimental repeats per mutant is noted in parentheses in FIG. 6; experiments were carried out in triplicate. Substitutions in the N-terminal third of ApoA-I significantly increased arylesterase activity approximately 30% in R10C, R27C, and R61C mutants (0.126±0.014; 0.125±0.018; 0.121±0.019 U/mg cell protein, respectively) compared to ApoA-I$_{WT}$ (0.095±0.013 U/mg cell protein). Conversely, as shown in FIG. 6, the K96C mutation had an approximate 30% reduction in arylesterase activity (0.067±0.011 U/mg cell protein) compared to ApoA-I$_{WT}$. R123C, R131C and K238C also showed evidence of increased PON arylesterase activity.

Cysteine substitutions in the C-terminal portion of ApoA-I, including ApoA-I$_{Paris}$ and ApoA-I$_{Milano}$ mutations ability to elevate secreted PON arylesterase activity (0.086±0.016; 0.076±0.029 U/mg cell protein, respectively) is not different from ApoA-I$_{WT}$ ability to elevate PON activity (0.095±0.013 U/mg cell protein) over conditioned media without ApoA-I (0.034±0.010).

EXAMPLE 9

Using ApoA-I Cysteine Variants for In Vivo Studies.

Studies using the ApoA-I cysteine variants of the invention should be conducted in mice. C57BL/6 mice would be the strain of choice, since it is susceptible to atherogenesis on a high fat diet (Oda et al., *Biochem Biophys Res Commun.* Jan. 25, 2002;290(3):921–7). Three classes of mice should be created: ones that are wild type, ones that bear a transgene that encodes wild type ApoA-I, and ones that bear a transgene that encode cysteine mutant forms of ApoA-I. This last group is further broken down into specific groups for each mutation. Care must be taken to maintain equivalent gene copy numbers so that direct comparisons can be made. Blood from these mice is drawn by tail vein bleeds. Paraoxonase levels can be measured by arylesterase activity measurements as described in Example 4.

If there is no noticeable change in paraoxonase activity, two things can be done, the first is to utilize a transgenic strain of mice in which the human variant of paraoxonase is expressed or modify the promoter for the APOAI transgene such that the gene expresses a greater amount of ApoA-I protein.

If an increase in paraoxonase activity is observed, then these mice can be either subjected to a high fat diet to see if indeed the addition of the ApoA-I mutant proteins is leading to protection against the onset of atherosclerosis. The lethality of organophosphate compounds should also be evaluated in these animals, since the ApoA-I mutant proteins may indirectly lead to protection against organophosphate poisoning.

The present examples, methods, procedures, treatments, specific compounds and molecules are meant to exemplify and illustrate the invention and should in no way be seen as limiting the scope of the invention. Any patents or publications mentioned in this specification are indicative of levels of those skilled in the art to which the patent pertains and are hereby incorporated by reference to the same extent as if each was specifically and individually incorporated by reference.

What is claimed is:

1. An isolated functional mutant Apolipoprotein A-I (Apo A-I) protein, comprising an amino acid sequence of SEQ ID NO:3, having a mutation comprising the substitution of at least one amino acid residue of said function mutant Apo A-I protein with cysteine at a residue position selected form the group consisting of 7, 10, 13, 17, 20, 22, 27, 30, 33, 39, 45, 49, 54, 58, 61, 96, 123, 131, 215, or 238, whereby said functional mutation ApoA-I protein has a specific effect on paraoxonase activity, wherein said functional mutant retains the amphipathic helical structure that is functionally required for mediating HDL assembly and determining HDL structure and composition.

2. The mutant Apo A-I protein of claim 1, wherein at least one cysteine substitution is selected from the group consisting of R10C, R27C, and R61C.

3. The mutant of Apo A-I protein of claim 1, wherein the mutant Apo A-I is expressed form a polynucleotide having a sequence of to SEQ ID NO:1, having at least one codon substitution encoding at least one cysteine substitution.

4. The mutant Apo A-I protein of claim 1 further comprising an affinity tag and a cleavage site.

5. The mutant Apo A-I protein of claim 4, wherein the functional mutant Apo A-I protein further comprises an affinity tag and a cleavage site having an amino acid sequence of SEQ ID NO:4, wherein the mutation comprising the substitution of at least one amino acid residue of said function mutant Apo A-I protein is substituted with a cysteine at a residue position selected form the group consisting of 18, 21, 24, 28, 31, 33, 38, 41, 44, 50, 56, 60, 65, 69, 72, 107, 134, 142, 226, or 249, whereby said functional mutation ApoA-I protein has a specific effect on paraoxonase activity.

6. The mutant of Apo A-I protein of claim 5, wherein the mutant of Apo A-I protein further comprises an affinity tag and a cleavage site is expressed from a polynucleotide having an optimized sequence of SEQ ID NO:2 having at least one condon substitution encoding at least one cysteine substitution.

7. The mutant Apo A-I protein of claim 3, wherein the polynucleotide is contained in a plasmid vector, wherein the vector is contained in a host cell.

8. The mutant Apo A-I protein of claim 6, wherein the polynucleotide is contained in a plasmid vector, wherein the vector is contained in a host cell.

9. The mutant Apo A-I protein of claim 1 further comprising a cysteine substitution at a residue position selected from the group consisting of 151 or 173.

10. The mutant Apo A-I protein of claim 5 further comprising a cysteine substitution at a residue position selected from the group consisting of 162 or 184.

11. A method of treating a disease selected from the group consisting of restenosis, atherosclerosis, and cardiovascular diseases, comprising the step of administering to a subject in need thereof a composition comprising an isolated polypeptide of claim 1.

12. A method of increasing arylesterase activity in a mixture comprising the step of adding to the mixture an ApoA-I mutant protein of claim 1 having a cysteine substitution selected from the group consisting of R10C, R27C and R61C.

13. A method of making an ApoA-I mutant protein having a cysteine substitution in a position with reference to SEQ ID NO: 3 of P7C, R10C, D13C, V17C, D20C, L22C, R27C, V30C, F33C, G39C, K45C, N49C, T54C, S58C, R61C, K96C, R123C, R131C, R215C arid K238C, comprising the steps of: culturing a host cell comprising a vector expressing said ApoA-I mutant protein: and separating said ApoA-I mutant protein from the host cell environment.

* * * * *

SEQUENCE LISTING

```
<160> NUMBER OF SEQ ID NOS: 4
<210> SEQ ID NO 1
<211> LENGTH: 897
<212> TYPE: DNA
<213> ORGANISM: Homo sapiens

<400> SEQUENCE: 1
agagactgcg agaaggaggt cccccacggc ccttcaggat gaaagctgcg gtgctgacct      60
tggccgtgct cttcctgacg gggagccagg ctcggcattt ctggcagcaa gatgaacccc     120
cccagagccc ctgggatcga gtgaaggacc tggccactgt gtacgtggat gtgctcaaag     180
acagcggcag agactatgtg tcccagtttg aaggctccgc cttgggaaaa cagctaaacc     240
taaagctcct tgacaactgg gacagcgtga cctccacctt cagcaagctg cgcgaacagc     300
tcggccctgt gacccaggag ttctgggata acctggaaaa ggagacagag ggcctgaggc     360
aggagatgag caaggatctg gaggaggtga aggccaaggt gcagccctac ctggacgact     420
tccagaagaa gtggcaggag gagatggagc tctaccgcca gaaggtggag ccgctgcgcg     480
cagagctcca gagggcgcg cgccagaagc tgcacgagct gcaagagaag ctgagcccac     540
tgggcgagga gatgcgcgac cgcgcgcgcg cccatgtgga cgcgctgcgc acgcatctgg     600 cccctacag cgacgagctg cgccagcgct tggccgcgcg ccttgaggct ctcaaggaga     660
acggcggcgc cagactggcc gagtaccacg ccaaggccac cgagcatctg agcacgctca     720
gcgagaaggc caagcccgcg ctcgaggacc tccgccaagg cctgctgccc gtgctggaga     780
gcttcaaggt cagcttcctg agcgctctcg aggagtacac taagaagctc aacacccagt     840
gaggcgcccg ccgccgcccc ccttcccggt gctcagaata aacgtttcca aagtggg       897

<210> SEQ ID NO 2
<211> LENGTH: 814
<212> TYPE: DNA
<213> ORGANISM: Artificial sequence
<220> FEATURE:
<223> OTHER INFORMATION: HUMAN GENETIC ORIGIN
<220> FEATURE:
```

```
<221> NAME/KEY: 5'UTR
<222> LOCATION: (1)..(18)
<223> OTHER INFORMATION: 5' UTR sequence containing Kpn I and Nde 1
      restriction sites
<220> FEATURE:
<221> NAME/KEY: misc_feature
<222> LOCATION: (22)..(29)
<223> OTHER INFORMATION: encodes His-6 affinity tag
<220> FEATURE:
<221> NAME/KEY: misc_feature
<222> LOCATION: (30)..(51)
<223> OTHER INFORMATION: Factor Xa Cleavage site
<220> FEATURE:
<221> NAME/KEY: misc_feature
<222> LOCATION: (92)..(97)
<223> OTHER INFORMATION: Bal I/Msc I restriction site
<220> FEATURE:
<221> NAME/KEY: misc_feature
<222> LOCATION: (126)..(131)
<223> OTHER INFORMATION: Ava I/Not I restriction site
<220> FEATURE:
<221> NAME/KEY: misc_feature
<222> LOCATION: (154)..(159)
<223> OTHER INFORMATION: BamHI restriction site
<220> FEATURE:
<221> NAME/KEY: misc_feature
<222> LOCATION: (181)..(186)
<223> OTHER INFORMATION: Afl II restriction site
<220> FEATURE:
<221> NAME/KEY: misc_feature
<222> LOCATION: (259)..(264)
<223> OTHER INFORMATION: EcoR I restriction site
<220> FEATURE:
<221> NAME/KEY: misc_feature
<222> LOCATION: (388)..(393)
<223> OTHER INFORMATION: Sac I restriction site
<220> FEATURE:
<221> NAME/KEY: misc_feature
<222> LOCATION: (427)..(432)
<223> OTHER INFORMATION: Pst I restriction site
<220> FEATURE:
<221> NAME/KEY: misc_feature
<222> LOCATION: (517)..(522)
<223> OTHER INFORMATION: Sal I restriction site
<220> FEATURE:
<221> NAME/KEY: misc_feature
<222> LOCATION: (608)..(613)
<223> OTHER INFORMATION: Apa I restriction site
<220> FEATURE:
<221> NAME/KEY: misc_feature
<222> LOCATION: (682)..(687)
<223> OTHER INFORMATION: Xho I restriction site
<220> FEATURE:
<221> NAME/KEY: misc_feature
<222> LOCATION: (766)..(771)
<223> OTHER INFORMATION: Hind III restriction site
<220> FEATURE:
<221> NAME/KEY: 3'UTR
<222> LOCATION: (784)..(814)
<223> OTHER INFORMATION: 3' UTR sequence containing Xba I, Spe I, Bgl
      II and Not I restriction sites

<400> SEQUENCE: 2
ggtaccaaaa gctggcatat gcatcaccat caccatcaca tcgaaggtcg tgacgagcca        60
ccgcagagtc cgtgggatcg cgtgaaggac ctggccactg tgtacgtgga tgtgctcaaa       120
gacagcggcc gcgactatgt gtctcagttt gaaggatccg ccttgggaaa acagctgaac       180
cttaagctcc ttgacaactg ggacagcgtg acctccacct tcagcaagct gcgcgaacag       240
ctcggccctg tgacccagga attctgggat aacctggaaa aggagacaga gggcctgcgc       300
caggagatga gcaaggatct ggaggaggtg aaggccaagg tgcagccgta cctggacgac       360
ttccagaaga gtggcagga ggagatggag ctctaccgcc agaaggtgga gccgctgcgc       420
gcagagctgc aggagggcgc gcgccagaag ctgcacgagc tgcaagagaa gctgagccca       480
```

```
ctgggcgagg agatgcgcga ccgcgcgcgc gcccatgtcg acgcgctgcg cacgcatctg        540
gccccgtaca gcgacgagct gcgccagcgc ttggccgcgc gccttgaggc tctcaaggag        600
aacggcgggg cccgcctggc cgagtaccac gccaaggcca ccgagcatct gagcacgctc        660
agcgagaagg ccaagccggc gctcgaggat ctgcgccagg gcctgctgcc ggtgctggag        720
agcttcaagg tcagcttcct gagcgctctg gaagagtaca ctaagaagct taacacccag        780
tgaggcgctc tagaactagt agatctgcgg ccgc                                    814
```

```
<210> SEQ ID NO 3
<211> LENGTH: 243
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: Pro or Cys (P7C)
<220> FEATURE:
<221> NAME/KEY: MISC_FEATURE
<222> LOCATION: (10)..(10)
<223> OTHER INFORMATION: Arg or Cys (R10C)
<220> FEATURE:
<221> NAME/KEY: MISC_FEATURE
<222> LOCATION: (13)..(13)
<223> OTHER INFORMATION: Asp or Cys (D13C)
<220> FEATURE:
<221> NAME/KEY: MISC_FEATURE
<222> LOCATION: (17)..(17)
<223> OTHER INFORMATION: Val or Cys (V17C)
<220> FEATURE:
<221> NAME/KEY: MISC_FEATURE
<222> LOCATION: (20)..(20)
<223> OTHER INFORMATION: Asp or Cys (D20C)
<220> FEATURE:
<221> NAME/KEY: MISC_FEATURE
<222> LOCATION: (22)..(22)
<223> OTHER INFORMATION: Leu or Cys (L22C)
<220> FEATURE:
<221> NAME/KEY: MISC_FEATURE
<222> LOCATION: (27)..(27)
<223> OTHER INFORMATION: Arg or Cys (R27C)
<220> FEATURE:
<221> NAME/KEY: MISC_FEATURE
<222> LOCATION: (30)..(30)
<223> OTHER INFORMATION: Val or Cys (V30C)
<220> FEATURE:
<221> NAME/KEY: MISC_FEATURE
<222> LOCATION: (33)..(33)
<223> OTHER INFORMATION: Phe or Cys (F33C)
<220> FEATURE:
<221> NAME/KEY: MISC_FEATURE
<222> LOCATION: (39)..(39)
<223> OTHER INFORMATION: Gly or Cys (G39C)
<220> FEATURE:
<221> NAME/KEY: MISC_FEATURE
<222> LOCATION: (45)..(45)
<223> OTHER INFORMATION: Lys or Cys (K45C)
<220> FEATURE:
<221> NAME/KEY: MISC_FEATURE
<222> LOCATION: (49)..(49)
<223> OTHER INFORMATION: Asn or Cys (N49C)
<220> FEATURE:
<221> NAME/KEY: MISC_FEATURE
<222> LOCATION: (54)..(54)
<223> OTHER INFORMATION: Thr or Cys (T54C)
<220> FEATURE:
<221> NAME/KEY: MISC_FEATURE
<222> LOCATION: (58)..(58)
<223> OTHER INFORMATION: Ser or Cys (S58C)
<220> FEATURE:
<221> NAME/KEY: MISC_FEATURE
<222> LOCATION: (61)..(61)
<223> OTHER INFORMATION: Arg or Cys (R61C)
<220> FEATURE:
```

<220> FEATURE:
<221> NAME/KEY: MISC_FEATURE
<222> LOCATION: (96)..(96)
<223> OTHER INFORMATION: Lys or Cys (K96C)
<220> FEATURE:
<221> NAME/KEY: MISC_FEATURE
<222> LOCATION: (123)..(123)
<223> OTHER INFORMATION: Arg or Cys (R123C)
<220> FEATURE:
<221> NAME/KEY: MISC_FEATURE
<222> LOCATION: (131)..(131)
<223> OTHER INFORMATION: Arg or Cys (R131C)
<220> FEATURE:
<221> NAME/KEY: MISC_FEATURE
<222> LOCATION: (151)..(151)
<223> OTHER INFORMATION: Arg or Cys (R151C)
<220> FEATURE:
<221> NAME/KEY: MISC_FEATURE
<222> LOCATION: (173)..(173)
<223> OTHER INFORMATION: Arg or Cys (173C)
<220> FEATURE:
<221> NAME/KEY: MISC_FEATURE
<222> LOCATION: (215)..(215)
<223> OTHER INFORMATION: Arg or Cys (R215C)
<220> FEATURE:
<221> NAME/KEY: MISC_FEATURE
<222> LOCATION: (238)..(238)
<223> OTHER INFORMATION: Lys or Cys (K238C)

<400> SEQUENCE: 3

```
Asp Glu Pro Pro Gln Ser Xaa Trp Asp Xaa Val Lys Xaa Leu Ala Thr
1               5                  10                  15

Xaa Tyr Val Xaa Val Xaa Lys Asp Ser Gly Xaa Asp Tyr Xaa Ser Gln
            20                  25                  30

Xaa Glu Gly Ser Ala Leu Xaa Lys Gln Leu Asn Leu Xaa Leu Leu Asp
        35                  40                  45

Xaa Trp Asp Ser Val Xaa Ser Thr Phe Xaa Lys Leu Xaa Glu Gln Leu
    50                  55                  60

Gly Pro Val Thr Gln Glu Phe Trp Asp Asn Leu Glu Lys Glu Thr Glu
65                  70                  75                  80

Gly Leu Arg Gln Glu Met Ser Lys Asp Leu Glu Glu Val Lys Ala Xaa
                85                  90                  95

Val Gln Pro Tyr Leu Asp Asp Phe Gln Lys Lys Trp Gln Glu Glu Met
            100                 105                 110

Glu Leu Tyr Arg Gln Lys Val Glu Pro Leu Xaa Ala Glu Leu Gln Glu
        115                 120                 125

Gly Ala Xaa Gln Lys Leu His Glu Leu Gln Glu Lys Leu Ser Pro Leu
    130                 135                 140

Gly Glu Glu Met Arg Asp Xaa Ala Arg Ala His Val Asp Ala Leu Arg
145                 150                 155                 160

Thr His Leu Ala Pro Tyr Ser Asp Glu Leu Arg Gln Xaa Leu Ala Ala
                165                 170                 175

Arg Leu Glu Ala Leu Lys Glu Asn Gly Gly Ala Arg Leu Ala Glu Tyr
            180                 185                 190

His Ala Lys Ala Thr Glu His Leu Ser Thr Leu Ser Glu Lys Ala Lys
        195                 200                 205

Pro Ala Leu Glu Asp Leu Xaa Gln Gly Leu Leu Pro Val Leu Glu Ser
    210                 215                 220

Phe Lys Val Ser Phe Leu Ser Ala Leu Glu Glu Tyr Thr Xaa Lys Leu
225                 230                 235                 240

Asn Thr Gln
```

<210> SEQ ID NO 4

```
<211> LENGTH: 254
<212> TYPE: PRT
<213> ORGANISM: Artificial sequence
<220> FEATURE:
<223> OTHER INFORMATION: HUMAN GENETIC ORIGIN
<220> FEATURE:
<221> NAME/KEY: INIT_MET
<222> LOCATION: (1)..(1)
<223> OTHER INFORMATION: Initiator Methionine
<220> FEATURE:
<221> NAME/KEY: SIGNAL
<222> LOCATION: (2)..(7)
<223> OTHER INFORMATION: His-6 affinity tag
<220> FEATURE:
<221> NAME/KEY: SITE
<222> LOCATION: (8)..(11)
<223> OTHER INFORMATION: Factor Xa Cleavage Site
<220> FEATURE:
<221> NAME/KEY: MISC_FEATURE
<222> LOCATION: (18)..(18)
<223> OTHER INFORMATION: Pro or Cys (P7C)
<220> FEATURE:
<221> NAME/KEY: MISC_FEATURE
<222> LOCATION: (21)..(21)
<223> OTHER INFORMATION: Arg or Cys (R10C)
<220> FEATURE:
<221> NAME/KEY: MISC_FEATURE
<222> LOCATION: (24)..(24)
<223> OTHER INFORMATION: Asp or Cys (D13C)
<220> FEATURE:
<221> NAME/KEY: MISC_FEATURE
<222> LOCATION: (28)..(28)
<223> OTHER INFORMATION: Val or Cys (V17C)
<220> FEATURE:
<221> NAME/KEY: MISC_FEATURE
<222> LOCATION: (31)..(31)
<223> OTHER INFORMATION: Asp or Cys (D20C)
<220> FEATURE:
<221> NAME/KEY: MISC_FEATURE
<222> LOCATION: (33)..(33)
<223> OTHER INFORMATION: Leu or Cys (L22C)
<220> FEATURE:
<221> NAME/KEY: MISC_FEATURE
<222> LOCATION: (38)..(38)
<223> OTHER INFORMATION: Arg or Cys (R27C)
<220> FEATURE:
<221> NAME/KEY: MISC_FEATURE
<222> LOCATION: (41)..(41)
<223> OTHER INFORMATION: Val or Cys (V30C)
<220> FEATURE:
<221> NAME/KEY: MISC_FEATURE
<222> LOCATION: (44)..(44)
<223> OTHER INFORMATION: Phe or Cys (F33C)
<220> FEATURE:
<221> NAME/KEY: MISC_FEATURE
<222> LOCATION: (50)..(50)
<223> OTHER INFORMATION: Gly or Cys (G39C)
<220> FEATURE:
<221> NAME/KEY: MISC_FEATURE
<222> LOCATION: (56)..(56)
<223> OTHER INFORMATION: Lys or Cys (K45C)
<220> FEATURE:
<221> NAME/KEY: MISC_FEATURE
<222> LOCATION: (60)..(60)
<223> OTHER INFORMATION: Asn or Cys (N49C)
<220> FEATURE:
<221> NAME/KEY: MISC_FEATURE
<222> LOCATION: (65)..(65)
<223> OTHER INFORMATION: Thr or Cys (T54C)
<220> FEATURE:
<221> NAME/KEY: MISC_FEATURE
<222> LOCATION: (69)..(69)
<223> OTHER INFORMATION: Ser or Cys (S58C)
<220> FEATURE:
<221> NAME/KEY: MISC_FEATURE
<222> LOCATION: (72)..(72)
<223> OTHER INFORMATION: Arg or Cys (R61C)
<220> FEATURE:
<221> NAME/KEY: MISC_FEATURE
```

```
<222> LOCATION: (107)..(107)
<223> OTHER INFORMATION: Lys or Cys (K96C)
<220> FEATURE:
<221> NAME/KEY: MISC_FEATURE
<222> LOCATION: (134)..(134)
<223> OTHER INFORMATION: Arg or Cys (R123C)
<220> FEATURE:
<221> NAME/KEY: MISC_FEATURE
<222> LOCATION: (142)..(142)
<223> OTHER INFORMATION: Arg or Cys (R131C)
<220> FEATURE:
<221> NAME/KEY: MISC_FEATURE
<222> LOCATION: (162)..(162)
<223> OTHER INFORMATION: Arg or Cys (R151C)
<220> FEATURE:
<221> NAME/KEY: MISC_FEATURE
<222> LOCATION: (184)..(184)
<223> OTHER INFORMATION: Arg or Cys (R173C)
<220> FEATURE:
<221> NAME/KEY: MISC_FEATURE
<222> LOCATION: (226)..(226)
<223> OTHER INFORMATION: Arg or Cys (R215C)
<220> FEATURE:
<221> NAME/KEY: MISC_FEATURE
<222> LOCATION: (249)..(249)
<223> OTHER INFORMATION: Lys or Cys (K238C)

<400> SEQUENCE: 4

Met His His His His His Ile Glu Gly Arg Asp Glu Pro Pro Gln
 1               5                  10                  15

Ser Xaa Trp Asp Xaa Val Lys Xaa Leu Ala Thr Xaa Tyr Val Xaa Val
            20                  25                  30

Xaa Lys Asp Ser Gly Xaa Asp Tyr Xaa Ser Gln Xaa Glu Gly Ser Ala
        35                  40                  45

Leu Xaa Lys Gln Leu Asn Leu Xaa Leu Leu Asp Xaa Trp Asp Ser Val
    50                  55                  60

Xaa Ser Thr Phe Xaa Lys Leu Xaa Glu Gln Leu Gly Pro Val Thr Gln
65                  70                  75                  80

Glu Phe Trp Asp Asn Leu Glu Lys Glu Thr Glu Gly Leu Arg Gln Glu
                85                  90                  95

Met Ser Lys Asp Leu Glu Glu Val Lys Ala Xaa Val Gln Pro Tyr Leu
            100                 105                 110

Asp Asp Phe Gln Lys Lys Trp Gln Glu Glu Met Glu Leu Tyr Arg Gln
        115                 120                 125

Lys Val Glu Pro Leu Xaa Ala Glu Leu Gln Glu Gly Ala Xaa Gln Lys
    130                 135                 140

Leu His Glu Leu Gln Glu Lys Leu Ser Pro Leu Gly Glu Glu Met Arg
145                 150                 155                 160

Asp Xaa Ala Arg Ala His Val Asp Ala Leu Arg Thr His Leu Ala Pro
                165                 170                 175

Tyr Ser Asp Glu Leu Arg Gln Xaa Leu Ala Ala Arg Leu Glu Ala Leu
            180                 185                 190

Lys Glu Asn Gly Gly Ala Arg Leu Ala Glu Tyr His Ala Lys Ala Thr
        195                 200                 205

Glu His Leu Ser Thr Leu Ser Glu Lys Ala Lys Pro Ala Leu Glu Asp
    210                 215                 220

Leu Xaa Gln Gly Leu Leu Pro Val Leu Glu Ser Phe Lys Val Ser Phe
225                 230                 235                 240

Leu Ser Ala Leu Glu Glu Tyr Thr Xaa Lys Leu Asn Thr Gln
                245                 250
```